(12) United States Patent
Xi et al.

(10) Patent No.: US 12,163,979 B2
(45) Date of Patent: Dec. 10, 2024

(54) NANO ROBOTIC SYSTEM FOR HIGH THROUGHPUT SINGLE CELL DNA SEQUENCING

(71) Applicants: VERSITECH LIMITED, Hong Kong (CN); City University of Hong Kong, Hong Kong (CN)

(72) Inventors: Ning Xi, Hong Kong (CN); Song Wang, Hong Kong (CN); Pengtao Liu, Hong Kong (CN); Zhiyong Sun, Hong Kong (CN); Lixin Dong, Hong Kong (CN); Chaojian Hou, Hong Kong (CN); Donglei Chen, Hong Kong (CN); Wenqi Zhang, Hong Kong (CN)

(73) Assignees: VERSITECH LIMITED, Hong Kong (CN); City University of Hong Kong, Hong Kong (CN)

(*) Notice: Subject to any disclaimer, the term of this patent is extended or adjusted under 35 U.S.C. 154(b) by 121 days.

(21) Appl. No.: 17/975,030

(22) Filed: Oct. 27, 2022

(65) Prior Publication Data
US 2023/0358782 A1    Nov. 9, 2023

Related U.S. Application Data

(60) Provisional application No. 63/276,805, filed on Nov. 8, 2021.

(51) Int. Cl.
*G01Q 30/02* (2010.01)
*C12Q 1/6869* (2018.01)
(Continued)

(52) U.S. Cl.
CPC .......... *G01Q 30/02* (2013.01); *C12Q 1/6869* (2013.01); *C23C 14/16* (2013.01); *C23C 14/165* (2013.01);
(Continued)

(58) Field of Classification Search
CPC ........ G01Q 30/02; G01Q 20/02; G01Q 30/20; G01Q 60/38; G01Q 70/16; C16B 40/20;
(Continued)

(56) References Cited

U.S. PATENT DOCUMENTS

| | | | | |
|---|---|---|---|---|
| 10,712,334 | B2* | 7/2020 | Choi | C12Q 1/6869 |
| 2014/0342394 | A1* | 11/2014 | Parker | G01N 33/5088 |
| | | | | 435/402 |
| 2019/0064110 | A1* | 2/2019 | Timp | G01N 33/6818 |

OTHER PUBLICATIONS

L. X. Dong, F. Arai, and T. Fukuda, "Electron-beam-induced deposition with carbon nanotube emitters," Applied Physics Letters, Sep. 2, 2002, vol. 81, No. 10, pp. 1919-1921.

L. X. Dong, F. Arai, and T. Fukuda, "Destructive constructions of nanostructures with carbon nanotubes through nanorobotic manipulation," IEEE/ASME Transactions on Mechatronics, Jun. 2004, vol. 9, No. 2, pp. 350-357.

(Continued)

*Primary Examiner* — Nicole M Ippolito
(74) *Attorney, Agent, or Firm* — Leason Ellis LLP

(57) ABSTRACT

A nano scale robotic system for single cell DNA sequencing of a strand of DNA positioned on a slide utilizes an atomic force microscope (AFM) having an end effector in the form of a cantilever with a tip. The AFM causes its cantilever tip to scan over the base pairs of the DNA strand. A pair of spaced-apart electrodes at the tip makes contact with opposite sides of the DNA strand and the current between bases of the DNA strand is measured by a current measurement system connected to the electrodes. An artificial intelligence-based data analytic system determines the DNA sequence based on the current from the current measuring system. The AFM tip is guided over the DNA strand by comparing compressed desired intensity local scan images and compressed actual intensity local scan images and using the difference to control the location of the tip.

27 Claims, 11 Drawing Sheets
Specification includes a Sequence Listing.

(51) Int. Cl.
| | |
|---|---|
| *C23C 14/16* | (2006.01) |
| *C23C 14/30* | (2006.01) |
| *C23C 14/34* | (2006.01) |
| *C23C 14/58* | (2006.01) |
| *C23C 16/04* | (2006.01) |
| *C23C 16/40* | (2006.01) |
| *C23C 16/56* | (2006.01) |
| *G01Q 20/02* | (2010.01) |
| *G01Q 30/20* | (2010.01) |
| *G01Q 60/38* | (2010.01) |
| *G01Q 70/16* | (2010.01) |
| *G03F 7/00* | (2006.01) |
| *G16B 40/20* | (2019.01) |

(52) U.S. Cl.
CPC .............. *C23C 14/30* (2013.01); *C23C 14/34* (2013.01); *C23C 14/588* (2013.01); *C23C 16/042* (2013.01); *C23C 16/402* (2013.01); *C23C 16/56* (2013.01); *G01Q 20/02* (2013.01); *G01Q 30/20* (2013.01); *G01Q 60/38* (2013.01); *G01Q 70/16* (2013.01); *G03F 7/0035* (2013.01); *G16B 40/20* (2019.02)

(58) Field of Classification Search
CPC ..... C12Q 1/6869; C23C 14/16; C23C 14/165; C23C 14/34; C23C 14/588; C23C 16/042; C23C 16/402; C23C 16/56; C21C 14/30; G03F 7/0035
See application file for complete search history.

(56) References Cited

OTHER PUBLICATIONS

L. X. Dong, L. Zhang, D. J. Bell, D. Grützmacher, and B. J. Nelson, "Nanorobotics for creating NEMS from 3D helical nanostructures," in Journal of Physics: Conference Series, 2007, vol. 61, pp. 257-261.

C. Hou, Y. Wang, L. Yang, B. Li, Z. Cao, Q. Zhang, Y. Wang, Z. Yang, and L. Dong, "Position sensitivity of optical nano-antenna arrays on optoelectronic devices," Nano Energy, 2018, vol. 53, pp. 734-744.

C Li, Y Cheng, S Bi, Y Cai, N Xi, "Learning object recognition based on compressive sampling", 2017 IEEE International Conference on Robotics and Biomimetics (ROBIO), Dec. 5-8, 2017, Macau, China, pp. 2663-2668.

Gongxin Li, Peng Li, Yuechao Wang, Wenxue Wang, Ning Xi, Lianqing Liu, "Efficient imaging and real-time display of scanning ion conductance microscopy based on block compressive sensing", International Journal of Optomechatronics, Jan. 2014, vol. 8, pp. 218-227.

Gongxin Li ; Wenxue Wang ; Yuechao Wang ; Shuai Yuan ; Wenguang Yang ; Ning Xi ; Lianqing Liu, "Nano-manipulation based on real-time compressive tracking" IEEE Transactions on Nanotechnology, Sep. 2015, vol. 14, No. 5, pp. 837-846.

B. Song, J. Zhao, N. Xi, H. Chen, K.W.C. Lai, R. Yang, L. Chen, "Compressive feedback-based motion control for nanomanipulation—theory and applications", IEEE Transactions on Robotics, Feb. 2014, vol. 30, No. 1, pp. 103-114.

Xi, N; Song, B; Yang, R; Lai, K W C; Chen, H; Qu, C; Chen, L, "Video rate atomic force microscopy: Use of compressive scanning for nanoscale video imaging", IEEE Nanotechnology Magazine, Mar. 2013, vol. 7, No. 1, pp. 4-8.

\* cited by examiner (a) Nano robot tracking a DNA strand.

(a) DNA strand tracking error.

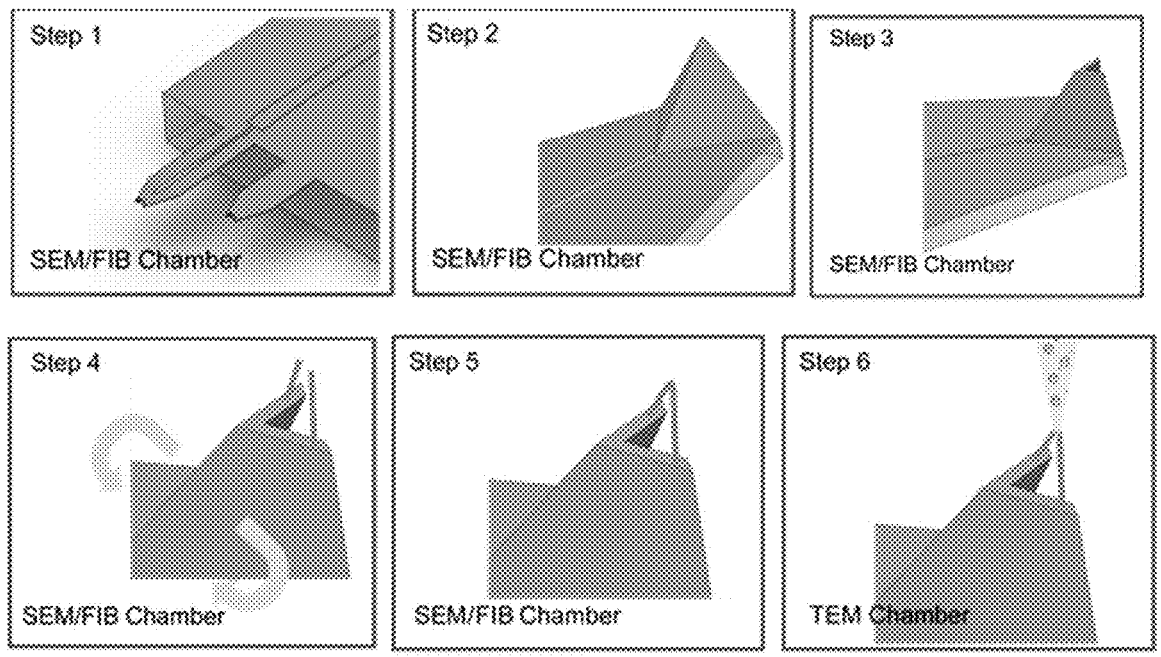
FIG. 7
FIG. 8A  FIG. 8B  FIG. 8C
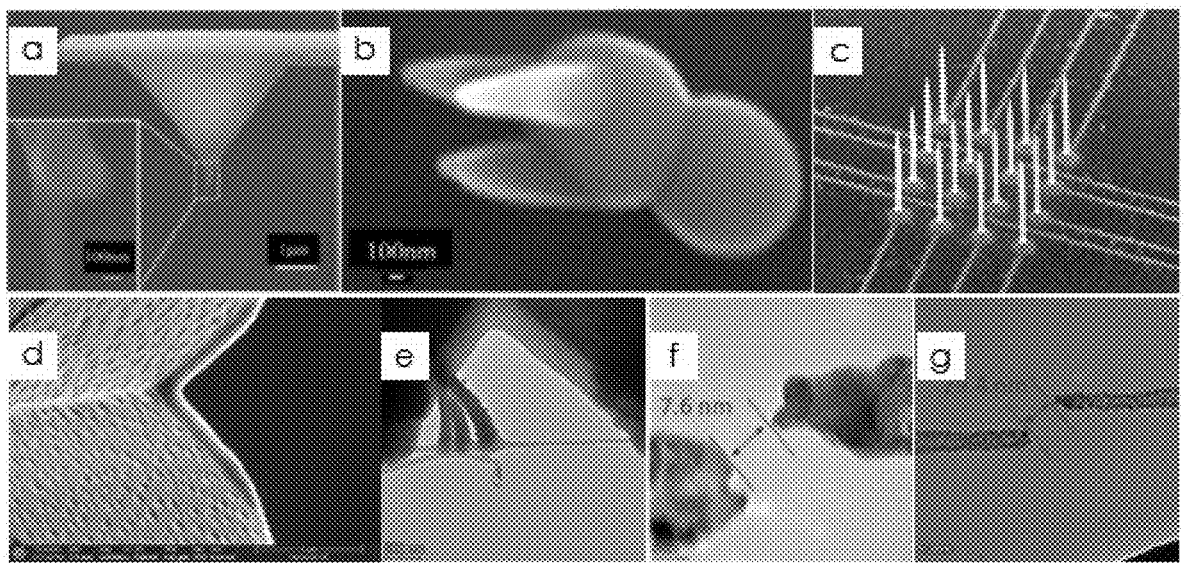
FIG. 8D  FIG. 8E  FIG. 8F  FIG. 8G FIG. 11A 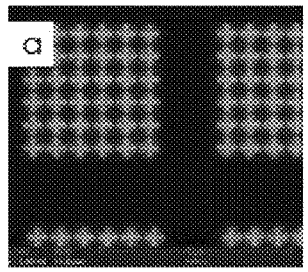 FIG. 11B 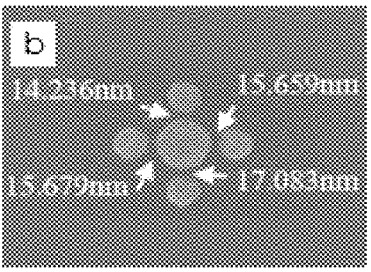 FIG. 11C 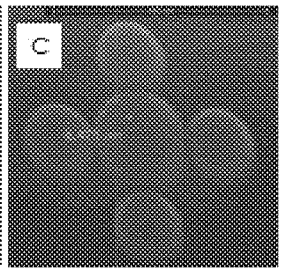 FIG. 11D 
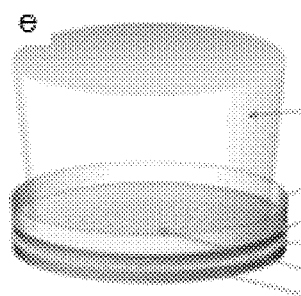
FIG. 11E
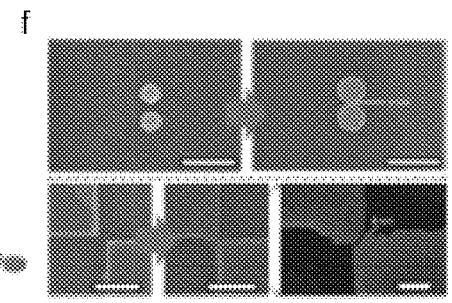
FIG. 11F
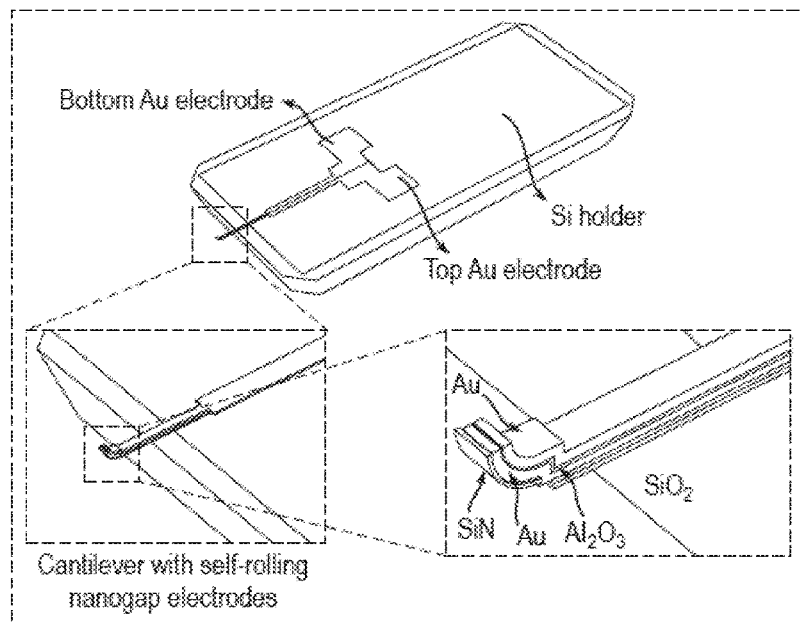
FIG. 12

FIG. 11A 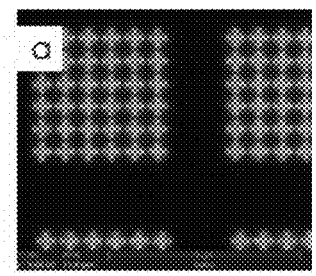 FIG. 11B 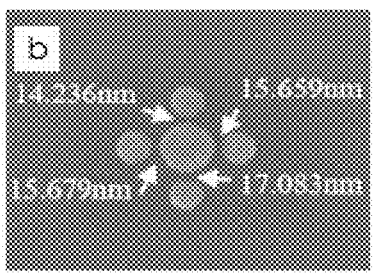 FIG. 11C 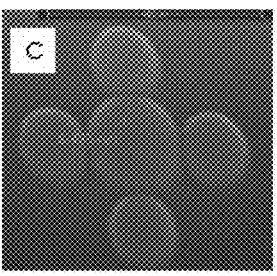 FIG. 11D 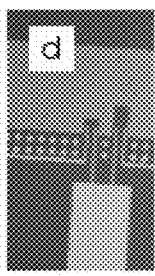
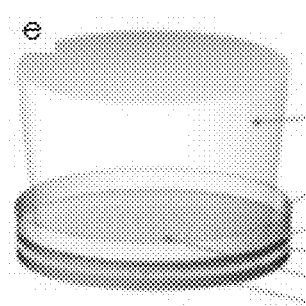 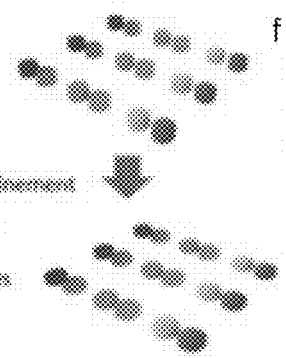 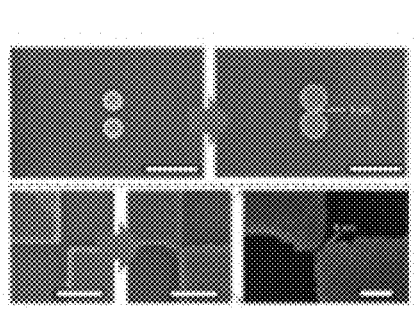
FIG. 11E            FIG. 11F
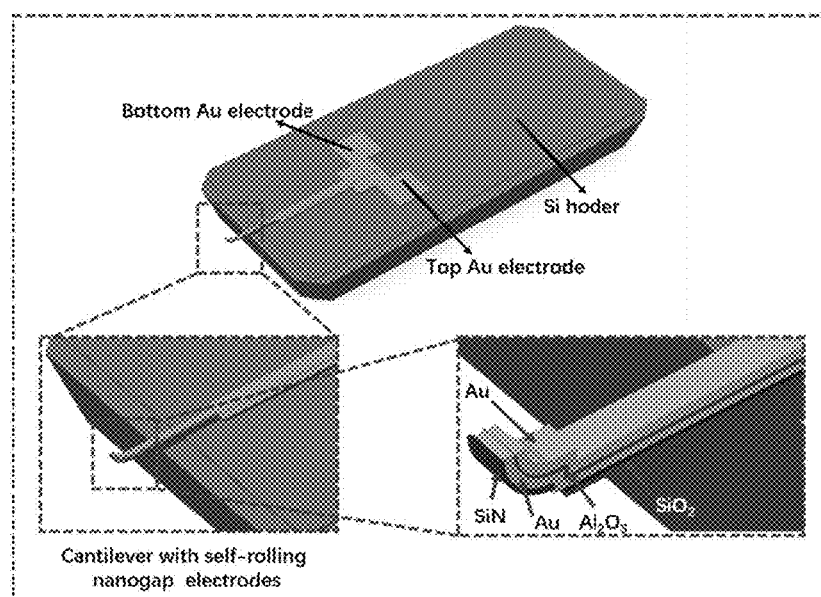
FIG. 12

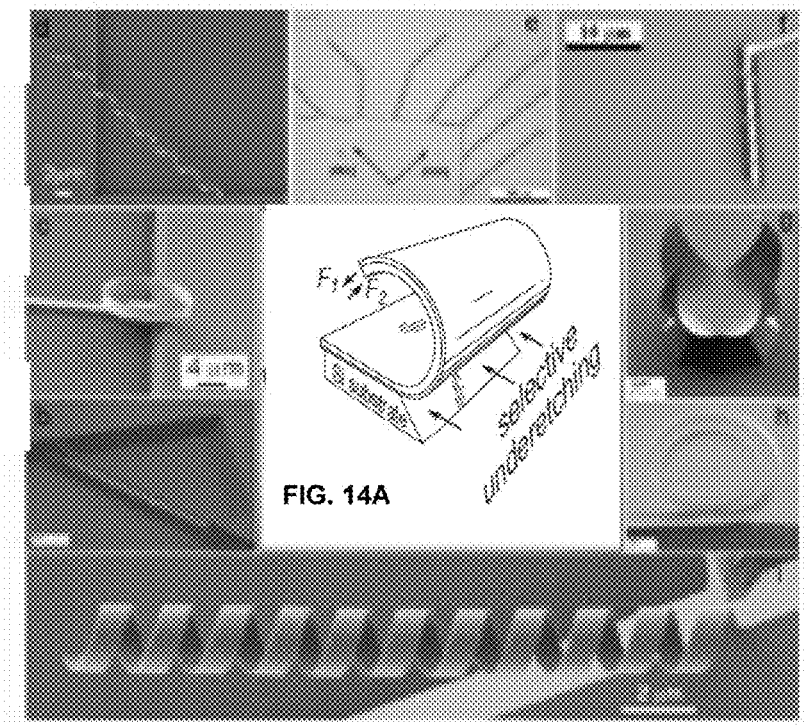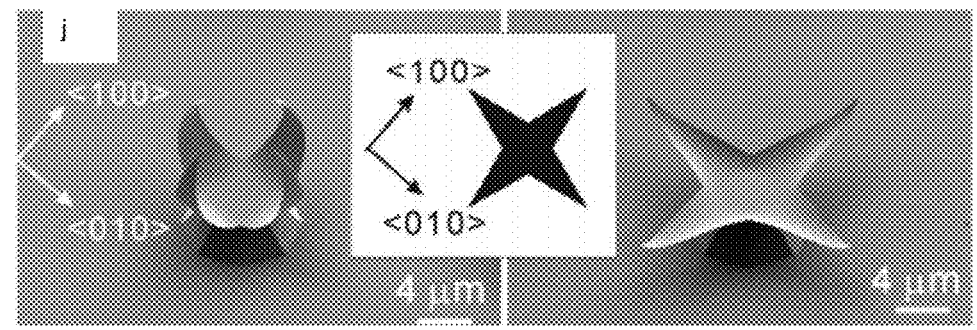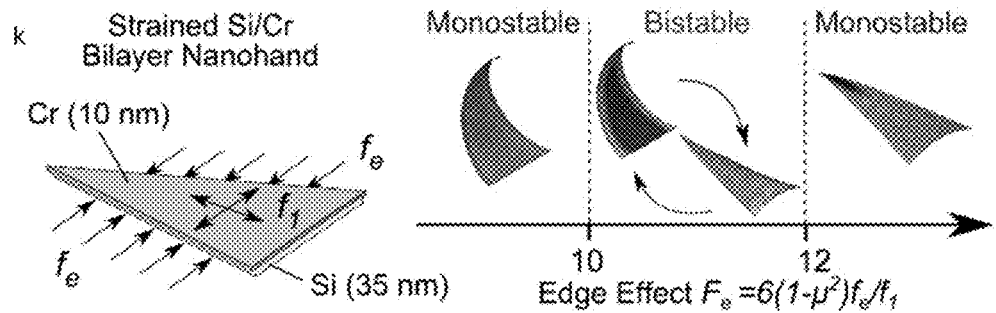

SEQUENCE LISTING

```
Sequence total quantity: 4
SEQ ID NO: 1            moltype = DNA  length = 30
FEATURE                 Location/Qualifiers
source                  1..30
                        mol_type = other DNA
                        organism = synthetic construct
SEQUENCE: 1
ttaccaatgc ttaatcagtg aggcacctat                                    30

SEQ ID NO: 2            moltype = DNA  length = 15
FEATURE                 Location/Qualifiers
source                  1..15
                        mol_type = other DNA
                        organism = synthetic construct
SEQUENCE: 2
ttaccaatgc ttaat                                                    15

SEQ ID NO: 3            moltype = DNA  length = 14
FEATURE                 Location/Qualifiers
source                  1..14
                        mol_type = other DNA
                        organism = synthetic construct
SEQUENCE: 3
ttttttttt tacc                                                      14

SEQ ID NO: 4            moltype = DNA  length = 14
FEATURE                 Location/Qualifiers
source                  1..14
                        mol_type = other DNA
                        organism = synthetic construct
SEQUENCE: 4
cctatttttt tttt                                                     14
```

NANO ROBOTIC SYSTEM FOR HIGH THROUGHPUT SINGLE CELL DNA SEQUENCING

CROSS-REFERENCE TO RELATED APPLICATION

The present application claims the benefit of priority to U.S. provisional patent application Ser. No. 63/276,805 filed Nov. 8, 2021, which is hereby incorporated herein by reference in its entirety.

SEQUENCE LISTING

The instant application contains a Sequence Listing which has been submitted electronically in XML format and is hereby incorporated by reference in its entirety. Said XML copy, created on Jul. 31, 2023, is named 04435_010270-US1_SL.xml and is 4,566 bytes in size.

FIELD OF THE INVENTION

The present invention relates to DNA sequencing, and more particularly to the use of Atomic Force Microscopy (AFM) based nano robotic systems and artificial intelligence for high throughput ingle cell DNA sequencing.

BACKGROUND OF THE INVENTION

DNA sequencing has become a key technology in many areas including biology, medicine and anthropology [JS2017]. Especially, single cell DNA sequencing is the foundation for new diagnostic methods, personal medicine as well as tissue engineering. The development of DNA sequencing technology plays a crucial role in dissecting the basic mechanisms in biological progress. Accompanied by the need for determining the molecular mechanisms that governs cell behaviors at the single cell level, the advances in the development of high throughput single cell sequencing technologies have been shown to obtain the nucleic information of the genomes or the transcriptomes of thousands of individual cells in a short time. This opens the black box of single cell identity, processing and connection. For example, high throughput single cell sequencing is applied in embryo development, stem cell biology, cancer, disease progression, etc. As a comprehensive recording of subpopulations and the change of cell states, high throughput single cell sequencing can provide insight into the molecular mechanism and the order of events. The application of high throughput single cell sequencing in stem cell biology has created a huge advance, especially in stem cell differentiation, cell renewal, reprogramming and embryo development.

The development of DNA sequencing technology has gone through over 40-years of history, including electrophoretic methods (the first generation, e.g., Sanger sequencing method), massively parallel methods (the second generation, e.g., Illumina's Hi-Seq genome sequencers), and the ongoing real-time, long-readable methods (the third generation, e.g., Oxford nanopore-based sequencers). Every breakthrough in the DNA sequencing technology has brought major technological leaps in the development of new diagnostics and treatments, and has had significant social and economic impacts.

The first and second generation of DNA sequencing technologies are mainly based on the polymerase chain reaction (PCR) method to chemically produce massive numbers of copies of the target DNA fragments to enable the identification of base-pairs in parallel. The base pair detection accuracy has reached more than 99.9%. In recent years, derivatives of the PCR-based DNA sequencing method, e.g., duplex sequencing protocol, has been developed to further enhance sequencing accuracy. The products in the market include bottleneck sequencing system (BotSeqS) [ML2016] and nano rate sequencing (NanoSeq) [FA2021].

However, PCR-based DNA sequencing methods are generally costly, time consuming and need lots of samples [SJ2020]. Furthermore, they can only sequence short-reads of base pairs (several hundreds) [PP2018, MT2019] and they rely on post processing to piece together the short strand sequences. Furthermore, the PCR-based sequencing is difficult for single cell sequencing that requires the extraction of available single cells from dead cells, which can cause the loss of the key information of some rare cell subpopulations [TL2016][SW2019][LC2020].

To conquer these problems, the third generation of DNA sequencing technologies are emerging. Among them, the most prevalent representative technique is the nanopore-based approaches [PP2018, MT2019, RR2019]. They employ either natural or synthetic nanometer pores or gaps to let the single DNA strand pass through, while recording the electric signal change of the part within the pore or gap for DNA bases decryption. As a result, a long DNA strand such as a strand directly from cells can be sequenced without PCR amplifications. The sample preparation is also relatively simple and the cost of sequencing is lower comparing to the first- and second-generation sequencing technologies. Currently, the commercially available nanopore based sequencing technology by Oxford Nanopore is based on bio-nanopores that utilize the transmembrane protein that possesses a natural capability of attracting small charged particles through its ion channel [JS2017, MT2019, CG2016]. The biological nanopore is inserted into a synthetic polymer membrane immersed in an electrolyte solution. Since the membrane normally exhibits fairly high electrical resistance, ions can only pass through the nanopore when an appropriate potential is applied across the membrane. When a single DNA strand enters the nanopore, it will cause distinctive disruptions in the ionic current, known as the "change of the conductance." This phenomenon is mainly attributed to the fact that the four bases: adenine (A), thymine (T), cytosine (C), and guanine (G), exhibit different electrostatic potentials [TO2006, LA2015, TO2012]. Furthermore some researchers also believe that the conductance of different bases is related to their geometrical properties rather than electronic characteristics [XG2006].

The bio-nanopores usually have natural and fixed geometrical dimensions and unstable morphology. They are environmentally sensitive and difficult to engineering/integrate into devices. Solid-state nanopore/nanogap-based techniques [PP2018] have also been considered and tried over the years. They have high robustness, less sensitivity to environmental conditions, as well as better ability to adjust the pore dimension and to integrate in arrays [JL2001, FT2013]. However, due to the limitation of fabrication technologies, it is still difficult to manufacture solid-state nanopores with market acceptable costs and yields.

Bio-nanopore sequencing technologies are generally facing several main challenges that induce measurement errors: First the speed of a DNA strand passing a nanopore is relative high (~0.5 cm/s) [PP2018] and cannot be controlled. It often causes missing bases and measurement noise. In addition, the DNA is in a liquid while the measurement is taken. This makes the electrical measurement more difficult.

Furthermore, a DNA strand can only pass the nanopore once and the measurement cannot be repeated. Thus, it is impossible to apply statistical and AI based methods to improve the measurement accuracy.

In addition, scanning probe microscopy (SPM) based approaches have also been applied to DNA sequencing. However due to the limitation on the motion control accuracy of SPM, it is difficult to precisely place the probe on a DNA base. The motion control requires sub-nano meter accuracy that has been impossible to achieve in the past. Furthermore, the limitations of available nano manufacturing technology have made it impossible to fabricate the required nano structures on a SPM probe for DNA sequencing.

One of the present inventors and his team have been working on developing and implementing Atomic Force Microscopy (AFM) based nanorobots for more than 20 years [XN2011]. This includes the development of basic techniques, such as on-line visualizing [XN2013], enhancing the nanomanipulation efficiency [LG2014, LG2015], accelerating the scanning rate [SB2014] as well as increasing the AFM positioning accuracy in the task space [XN2013]. In addition, AFM-based nanorobots have been successfully applied to manufacturing CNT-based IR sensors [FC2009, CH2010], and the biomedical studies [YR2015].

However, the current AFM motion control available in the market relies on position sensors. Due to system drift and probe deformation, it is impossible to directly measure the tip position in sub-nanometer scale with such systems. Furthermore, visual tracking methods required to obtain the position result in errors in the vector space. Therefore, feature extraction from images is required to determine and correct for the errors. This process is time-consuming if the features of the images are not explicit.

Although featureless methods have been proposed, two critical problems still exist. First, since the problem is still formulated in the vector space, these methods require a complicated calibration process, which is extremely difficult to carry out when high precision is required, such as nanoscale motion control. Second, all of the featureless methods require the whole image for successful feedback control, which is time consuming for systems with slow sensor feedback, such as an AFM which can only obtain an image by scanning pixel by pixel. Thus, the challenge is to develop a new AFM image-based motion control method to achieve sub-nanometer motion accuracy.

SUMMARY OF THE INVENTION

The nano robotic system of the present invention is based on recent breakthroughs in nano robot motion control, nano fabrications and AI-based data analytics to overcome the difficulties in third generation DNA sequencing technology. As a result, the robotic system of the present invention is able to achieve sub-nano meter position measurement without a liquid environment, controllable measurement speed and multiple measurements. Thus, the measurement accuracy is significantly improved and the cost of sequencing is reduced several folds. The single cell sequencing is faster and more convenient.

The system of the present invention includes an Atomic Force Microscopy (AFM) based nano robotic manipulator, a high precision tunnelling current measurement system, a nano robot end effector, and artificial intelligence (AI) based data analytic system. The robot motion is controlled by a novel semantic compressive feedback control system capable of sub-nano meter motion tracking accuracy. The nano robotic manipulator is equipped with the end effectors that can measure the current between two bases. A single strand DNA molecule is fixed on a slide or substrate, such as mica, and the nano robot moves the end effector along the DNA molecule and measures the current between the two base contact points. The measurement data is analyzed by a novel Generative Adversarial Tri-model (GAT) machining learning scheme in order to obtain the DNA sequence. The measurement can be repeated multiple times until sufficient measurement data is obtained to reach required confidence in the result.

The newly developed semantic compressive motion control overcomes the major problems in traditional image-based control by eliminating feature extractions, system calibrations for establishing coordinate transformation, and high computation needs for image processing and pattern recognition. Further, the system uses a non-vector space control approach. Considering local scan images as sets, the motion control problem is formulated in the space of local scan image sets, instead of traditional vectors. In this way, all the intensity information in the image will be used for control. Therefore, no feature extraction is needed. Since the problem is formulated in the space of sets, the complicated calibration process is not required. Second, the non-vector space control can also work with compressive feedback, i.e., feedback with compressed information such as compressed images. As a result, both the sampling and computation time can be significantly reduced, and the system can have a faster feedback rate, which is crucial to high accuracy motion control.

BRIEF DESCRIPTION OF THE DRAWINGS

The foregoing and other objects and advantages of the present invention will become more apparent when considered in connection with the following detailed description and appended drawings in which like designations denote like elements in the various views, and wherein:

FIG. 5 illustrates the experimental results of Nano robot end-effector tracking a DNA strand with the embodiment of FIG. 4 where

FIG. 7 is a series of images showing the sequence of steps in fabricating a prototypes of sub-10-nm-gap dual-tip AFM cantilevers.

FIG. 8 shows images of the preliminary results of the fabrication of FIG. 7 where FIG. 8A shows the use of EBID to solder a carbon nanotube on the tip of an AFM cantilever, FIG. 8B shows the growth of fingers on a polystyrene dimer, FIG. 8C shows large aspect ratio (>20) nanowires in a 4×4 arrays, FIG. 8D illustrates a FIB used to fabricate an array of 100 nm diameter base discs with a 500 nm pitch in between and 50-nm-wide on-chip leads on a Si+SiO$_2$ substrate coated with a gold film, FIG. 8E shows a flat AFM cantilever tip successfully achieved using the processes shown in FIG. 7, steps 1-3 using Focused-Ion-Beam Chemical Vapor Deposition (FIBCVD) and cutting, FIG. 8F shows a nanotube bridged between the flats and cut with the e-beam of a TEM, and FIG. 8G shows that an initial gap of 7.6 nm has been achieved;

FIG. 11A is an image of an optical antenna array of pentamer discs, FIG. 11B is an enlarged view of FIG. 11A with gap dimensions, FIG. 11C is a further enlarged view of the discs: FIG. 11D shows optical antennas from special processes with a sub-10-nm gap, FIG. 11E illustrates a cantilever chip with an optical antennas on it, FIG. 11F shows a sequence of images illustrating laser stamping;

FIG. 12 is a series of schematic drawings of the design of sub-10-nm-gap dual-tip AFM cantilevers based on strain engineering;

FIGS. 14A to FIG. 14I show curled up designs for helical structures, and FIG. 14J and FIG. 14K show bistable curled-up claws that can serve as cantilevers;

FIG. 15 is a nano robot end-effector fabrication;

FIG. 16 is a practical measurement scenario using the nano robot disclosing SEQ ID NO: 2;

FIG. 17 is an equivalent battery chain model for a DNA chain disclosing SEQ ID NO: 2;

FIG. 18 is a point contact approximation between electrodes and a DNA chain disclosing SEQ ID NO: 2;

FIG. 19 is a concatenation of T nucleobases at the beginning and end of a DNA chain disclosing SEQ ID NOS 3 and 4, respectively, in order of appearance;

FIG. 20 is an ideal equation about the DNA sequence based on measurement values;

FIG. 21 is an illustration of nano robot motion error disclosing SEQ ID NO: 2;

FIG. 22 is an actual measurement matrix with beta noise;

FIG. 23 shows actual equations about DNA sequence based on measurements with noise;

FIG. 24 is the structure of a neural network used to solve the overdetermined equation;

FIG. 25 is a flow chart of a DNA iterative sequencing framework;

FIG. 26 is a graph of DNA sequencing accuracy under pure Gaussian contact noise;

FIG. 27 is a graph of DNA sequencing accuracy under pure beta motion error from the nano robot motion;

FIG. 28 is a graph of DNA sequencing accuracy under joint contact noise and motion error;

FIG. 29 is a schematic diagram of the Generative Adversarial Tri-model (GAT) model;

FIG. 30 is a diagram of a neural network structure used in the GAT model (left) and an illustration of the method to reproduce an arbitrary function (right); and FIG. 31 is a diagram of the GAT model for noise calibration.

DETAILED DESCRIPTION OF THE INVENTION

Figure 1:
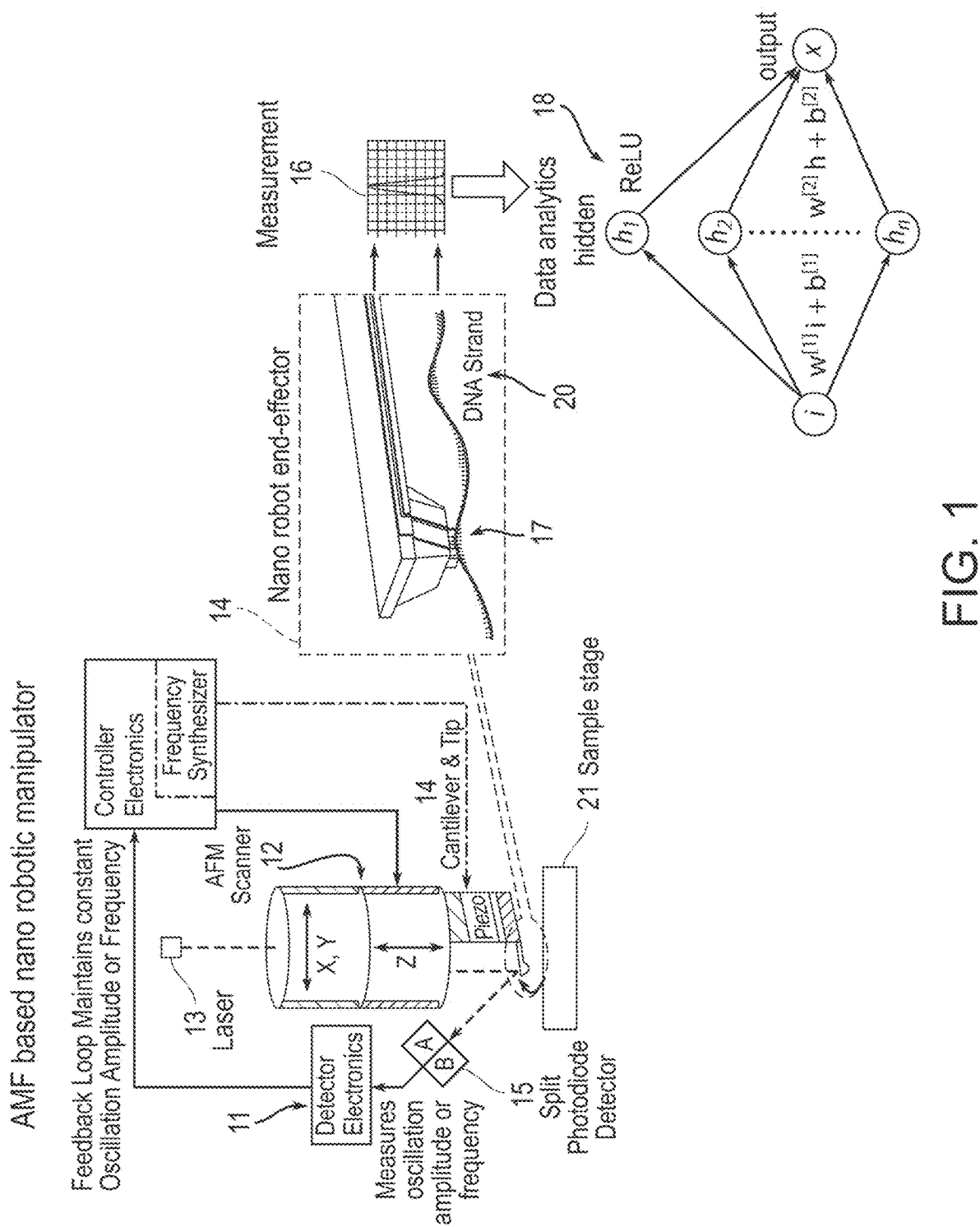
FIG. 1 is an Atomic Force Microscopy (AFM) based nano robotic system for DNA sequencing according to the present invention.

As shown in FIG. 1, the system of the present invention includes an Atomic Force Microscopy (AFM) based nano robotic scanner or manipulator 12, a nano robot end effector 14 positioned above the stage of the AFM and moved by it, a high precision tunnelling current measurement system 16 and an AI based data analytic system 18. An AFM system includes an atomic force microscope which provides various types of surface measurements that meet the needs of scientists and engineers. It is powerful because an AFM can generate images at atomic resolution with angstrom scale resolution height information, with minimum sample preparation. An AFM uses an end-effector in the form of a cantilever with a very sharp tip 17 to scan over a sample surface. As the tip approaches the surface the close-range attractive force between the surface and the tip causes the cantilever to deflect towards the surface. However, as the cantilever is brought even closer to the surface, such that the tip makes contact with it, increasingly repulsive force takes over and cause the cantilever to deflect away from the surface.

A laser beam from a laser 13 is used to detect cantilever deflections towards or away from the surface. By reflecting an incident beam off the flat top of the cantilever, any cantilever deflection will cause slight changes in the direction of the reflected beam. A position-sensitive photo diode (PSPD) 15 can receive the reflected light beam, which can be used to track changes in the deflection (Z axis) of the cantilever. Thus, if an AFM tip passes over a raised surface feature, the resulting cantilever deflection (and the subsequent change in direction of reflected beam) can recorded by the PSPD.

An AFM images the topography of a sample surface by scanning the cantilever over a region of interest (X and Y axes). The raised and lowered features on the sample surface influence the deflection of the cantilever, which is monitored by the PSPD. By using a feedback loop through detector electronics 11 and controller electronics 19 the height of the tip above the surface can be controlled—thus maintaining constant laser position—and the AFM can generate an accurate topographic map of the surface features.

In the present invention, the robot motion control is a novel semantic compressive feedback control system. Semantic compression is a process whereby the representation of the information, such as sensory data, is compressed/simplified, i.e. the amount of data representing the information is reduced based on the semantic content, i.e. the meaning of the information. The semantic feedback control is feeds back the semantic compressed sensory data instead of original sensory data.

The semantic compressive feedback control of the present invention is capable of sub-nano meter motion tracking accuracy not only in the vertical direction but so as to scan over a DNA sample strand 20 on a sample stage 21 of the microscope. The end effector 16 can measure the current between bases of a DNA strand. A single strand DNA molecule 20 is fixed on a substrate, such as mica, that is located in the sample stage. The nano robot or scanner 12 moves the end effector 16 along the DNA molecule and measures the current between two contact points on either side of the DNA molecule. The measurement data is analyzed by a novel Generative Adversarial Tri-model (GAT) machining learning scheme of the analytic system 18 in order to obtain the DNA sequence.

It should be noted that the measurement is done without a liquid environment, and the speed of the movement of the nano robot manipulator can be optimized and controlled to achieve reliable current measurement. More importantly, the measurement can be repeated multiple times until sufficient measurement data is obtained to reach the required confidence in the measurement result.

Positioning of the end effectors along the DNA strand is achieved with the newly developed semantic compressive motion control of the present invention. This motion control system has successfully overcome the major problems in traditional image-based control by eliminating feature extractions, system calibrations for establishing coordinate transformation, and high computation needs for image processing and pattern recognition.

Figure 2:
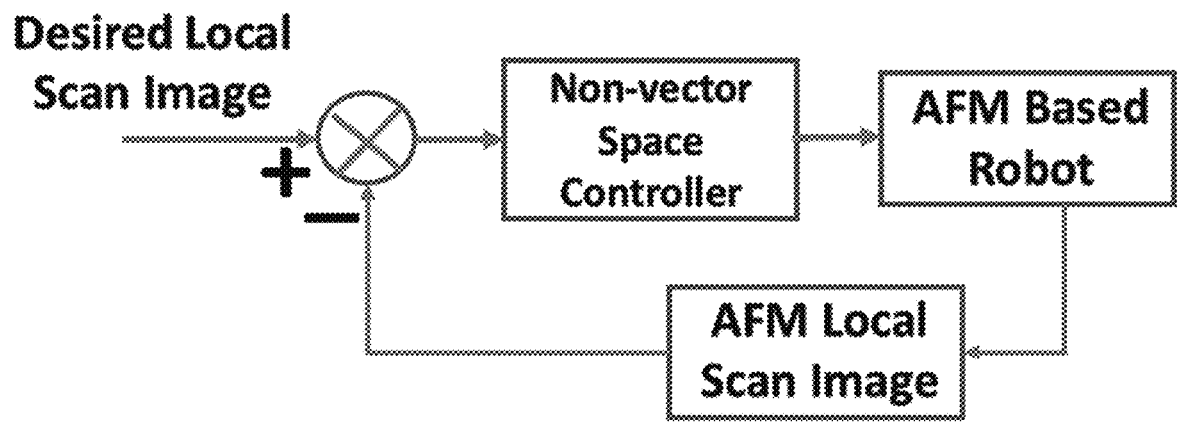
FIG. 2 is a non-vector space motion control based local scan control according to the present invention.

To address the shortcomings of the prior art, the present invention relies on a newly developed non-vector space control approach as shown in FIG. 2. Considering local scan images as sets, the motion control problem can be formulated in the space of local scan image sets instead of traditional vectors. In this way, all the intensity information in the image will be used for control. Therefore, no feature extraction is needed. Since the problem is formulated in the space of sets, the complicated calibration process is not required. Second, the non-vector space control can also work with compressive feedback, i.e., feedback with compressed information such as compressed images. As a result, both the sampling and computation time can be significantly reduced. Thus, the system can have a faster feedback rate, which is crucial to high accuracy motion control.

Figure 3:
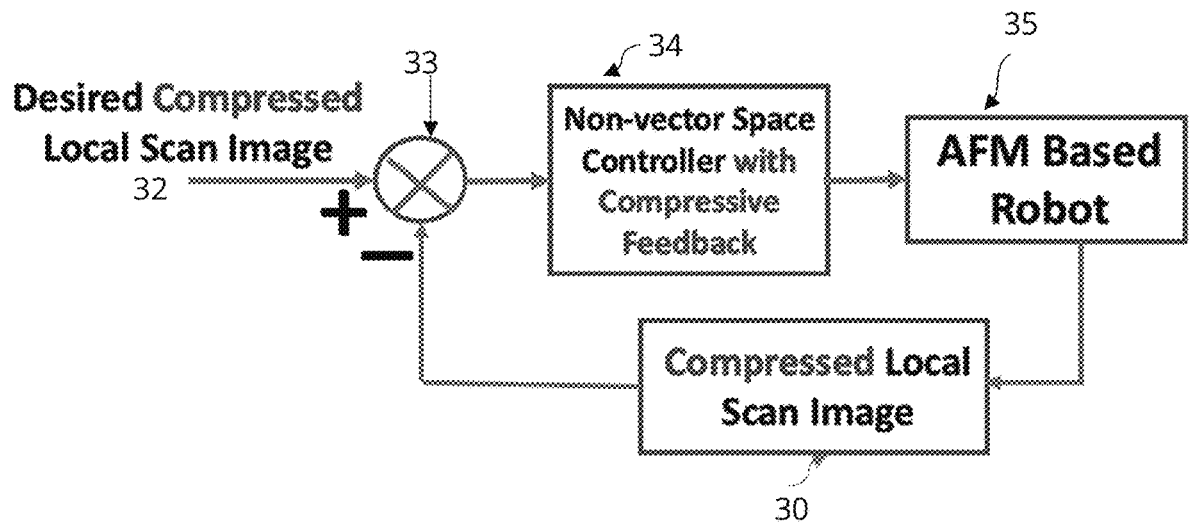
FIG. 3 is a non-vector space motion control based on compressed local scan images.

The general schematic of non-vector space control under compressive feedback is shown in FIG. 3. The difference from the full local scan image feedback is that both the goal and feedback of local scan images are compressed. The sensing in the compressive feedback is a new paradigm of signal acquisition. Instead of sampling the signal directly, it samples the signal in its compressed form. Then the system relies on advanced optimization or greedy algorithms to recover the original signal [XN2007]. In the AFM scanning process, instead of performing traditional zigzag scanning, a compressive scan pattern is used to obtain compressed local scan images that have much less data and can be performed at a much higher rate compared to full scanning [XN2013] [SB2014], [LG2014] [LG2015]. Furthermore, in the local scan images a prior knowledge of the content of the images, such as a DNA strand to be measured, are usually available. Semantic compressive sensing has been developed to utilize knowledge of the content to improve the sampling [LC2017] [LC2018].

A non-vector space control method can be based on compressive feedback as shown in FIG. 3. The term "non-vector space" means the control is not performed in traditional vector space but in the space of sets. Zhao et al., "Compressive feedback based non-vector space control," American Control Conference (June 2012). Consider an initial set of compressed actual local scan images 30 and a goal or desired set 32, a stabilizing non-vector space controller 34 is designed to make the set dynamics converge to the goal set. The difference between the actual compressed images 30 and the desired or goal images 32 is determined in subtractor or comparator 33. This difference signal is applied to the controller 34, which in turn drives the AFM based robot 35 so that the actual local image approaches alignment with the goal image because of the feedback loop. Because of the compressive feedback the controller works even when only partial elements of the feedback set are available; that is, the same controller can still stabilize the set dynamics around the goal set with the compressive feedback. The controller is applied to visual servoing (vision-based robot control) by considering images as sets. In this way, image processing for feature extraction is not required, which is an essential process in conventional servo methods. Moreover, the compressive feedback can reduce the size of feedback image. This is important when the sampling process is time consuming, such as imaging using atomic force microscopy (AFM). The visual servoing formulation of the controller is further applied to the motion control in nanomanipulations. Simulation results suggest good performance of the controller. The framework proposed can be extended to other systems where the signals can be represented as sets.

Inspired by the recent development in neuroscience, in a primate brain the identity of objects is represented in the infratemporal cortex and is invariant to different transformations that do not affect the object identity [BS2004]. Recently, Chang et al. [CL2017] proposed an axis model to study how a primate encodes and decodes facial identity. They found that in the primate brain, a human face is represented by very simple neural codes which correspond to facial content along specific axes in the face space. A face image is able to be linearly recovered with the responses of approximately 200 cells, and different cells carry complementary face information for reconstruction.

Based the axis model in [CL2017], in a primate brain, objects of the same class have similar and even the same features, and images of an object are expressed linearly through a number of content-associated axes. For instance, faces of different people have common visual structures, i.e., eyes, mouths, and noses, and their relative locations are similar. Hence, images can be reasonably represented with some common high-level parts [MN2015]. This is the foundation of semantic compression.

For local images in an AFM motion, specific common semantic contents exist. This fact leads to a low rank representation of the image [LC2017] Therefore, common semantic contents are extracted and emphasized during the compressive sampling. The semantic compressive scanning method utilizes a sensing matrix learned from a group of images of DNA strands. The sensing matrix training process can be conducted through various approaches, such as the prevalent deep learning strategy [LC2017]. In order to achieve efficient low-rank representation of local scan AFM images of DNA strands, the non-negative matrix factorization (NMF) [LC2018] representation is used to learn the semantic content of AFM images of DNA strands.

By applying the semantic compressive feedback, a high rate of feedback control with AFM local scan images is achieved. It enables the nano robot end effector to achieve a high precision tracking of DNA strands for measurements. The present inventors have implemented and experimentally tested semantic compressive feedback control in an AFM based nano robotic system as shown in FIG. 4. The experimental results, as shown in FIG. 5, where FIG. 5A shows the robot end-effector on DNA strands and FIG. 5B shows the DNA strand tracking error, have demonstrated that a sub-nano meter tracking accuracy for a DNA strand has been achieved. This lays down the foundation to use the nano robotic system for DNA sequencing.

Figures 4A, 4B:
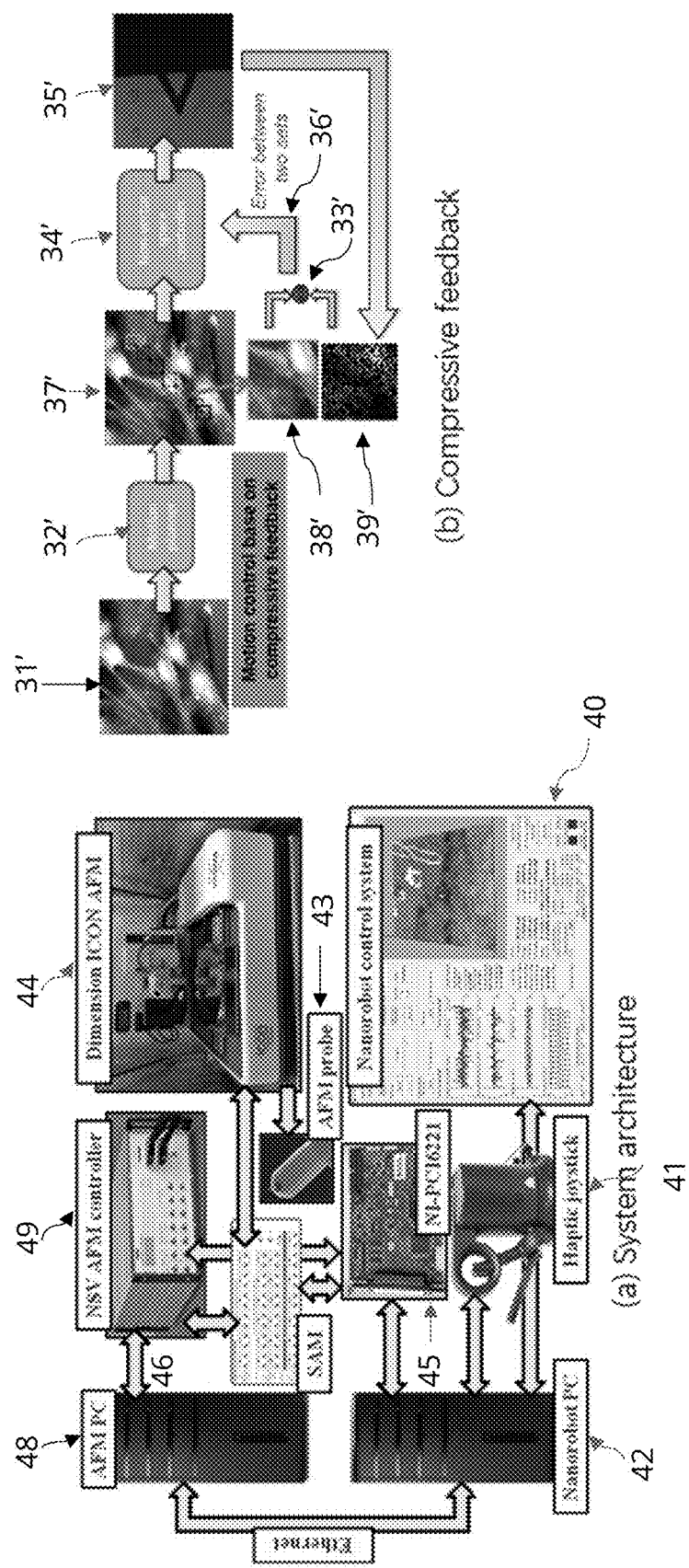
FIG. 4A is block diagram of the system architecture of an embodiment of an AFM based nano robotic system with semantic compressive feedback and FIG. 4B is a flow diagram of the operation of the system while using compressive feedback according to the present invention.
Figure 5A:
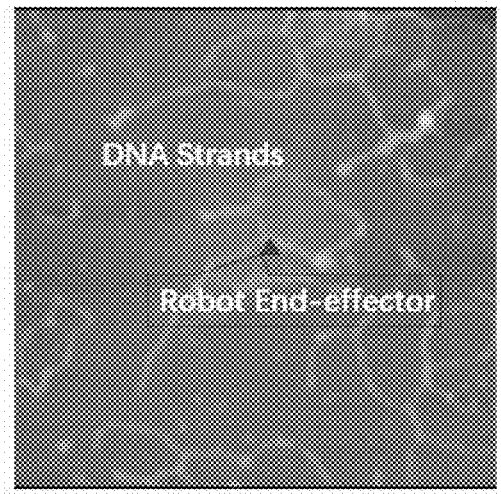
FIG. 5A shows the robot end-effector on DNA strands and FIG. 5B shows the DNA strand tracking error.
Figure 5B:
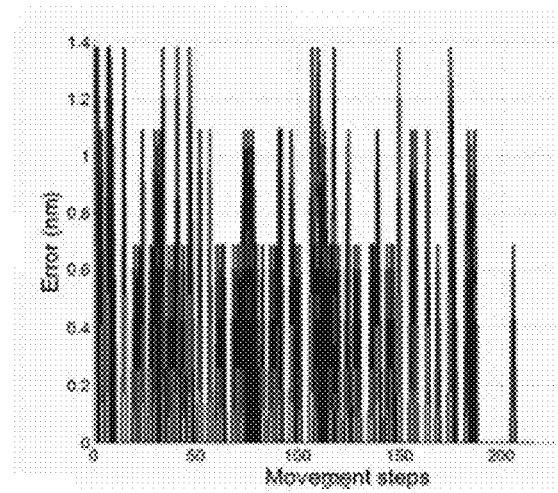

FIGS. 4A and 4B are hardware and block diagram/image equivalents to FIG. 3. As noted with respect to FIG. 3, in the prior art the positioning of the tip along a DNA strand was done in vector space, i.e., on the basis of the location of the tip in X, Y, Z coordinates. However, the distances required for the present invention are too small for this to be effective. Instead the present invention employs a novel technique using non-vector space. With this new control process an image of only the local area near the tip is formed. Thus, the amount of data is greatly reduced over a system that utilizes the entire image. Then this local image is subjected to semantic compression to further reduce the amount of data. A semantically compressed desired image of a local portion of the strand is also formed from repeated prior scans. Then the actual local compressed image is compared to the desired or ideal local compressed image, and the difference is the control error signal that is fed back to AFM to control the movement of the tip to the desired location as represented by the compressed ideal local image. By using image comparison there is no need to use vector space coordinates. By using local images, the amount of data and the time it takes to process it, is greatly reduced. Further, the amount of data is further reduced by using sematic compress on the local images, both actual and desired.

In the arrangement of FIG. 4A the AFM includes probe 43, microscope platform 44, its controller 49 and its processor 48. Signal access module (SAM) 46 provides access to the signals in the AFM controller 49 such as voltages on the actuators, laser deflection signals from photo detectors, etc. and also allows commands to be sent to the controller 49 and microscope platform 44. The device 45 is an I/O or interface board with a digital to analog converter. The tip or probe motion control system includes control system 40, haptic joystick 41 and programs stored in Nanorobot PC 42. System 40 is a software interface to the system with a display for the images, information about the system and the ability to diagnose problems. As indicated by the Ethernet line, these processors can work in parallel with each other, sharing information. It may also be possible to have the functions of PC 42 run within PC 48, which is the processor supplied by the vendor of the AFM.

The desired (goal) local scan images are created from AFM local images of the DNA obtained in a prior scan. These images are stored in Nanorobot PC 42. From I/O device 45 the images pass through Nanorobot PC 42 to the control system 40.

As the probe 43 is moved over the strand of DNA on the substrate under the control of the joystick 41 or by means of autonomous scanning, actual local images are taken by the AFM 44. These images are made accessible to Nanorobot PC 42 through SAM 46 and D/A converter 45. In that processor the images are semantically compressed. The comparison of the semantically compressed desired images previously stored in that processor 42 and the actual local compressed images is formed by Nanorobot PC 42 and AFM PC 48. The processor 42 sends the difference signal back to controller 49, which is a non-vector space controller 34', through converter 45 and SAM 46 to correct for motion errors.

Control system 40 and/or joystick 41 form the motion planner 32' of FIG. 4B. The ideal image 31' is compressed in planner 32' to form the compressed image 37'. A local portion of it 38' is passed to the comparator 33'. The actual local compressed images come from the AFM 35' and a compressed local portion 39' of it are also passed to comparator 33'. The results of the comparison (error) 36' are delivered to non-vector space controller 34". The output of controller 34' is applied to the motion control of AFM 35' to vary the position of the probe in a feedback loop that stabilizes its position along the DNA strand.

Figure 6A:
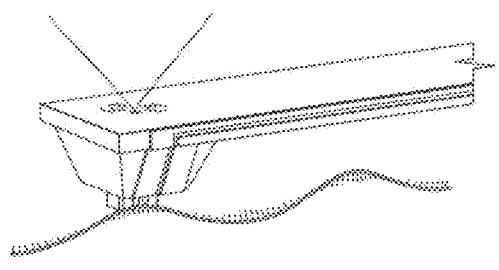
FIG. 6A illustrates the structure of an AFM cantilever and FIG. 6B illustrates sub-10 nm-separation electrodes and the objective parameters of the AFM cantilever.
Figure 6B:
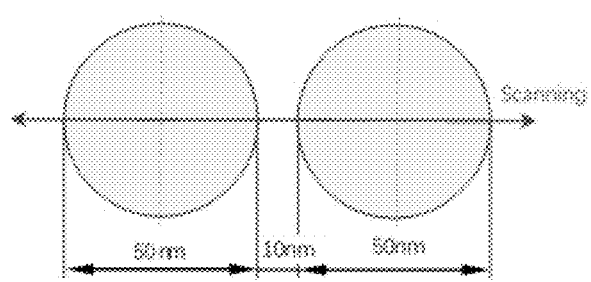

In order to carry out the invention, AFM cantilevers with dual cylindric nanoelectrodes are required to be fabricated on their pyramid/cone tips as shown in FIG. 6, where FIG. 6A illustrates the structure of an AFM cantilever and FIG. 6B illustrates sub 10 nm-separation electrodes and the objective parameters of the AFM cantilever. The cylindrical metal tips are specified as having sub-10 nm separations, 50 nm or smaller in diameters, and 45 nm in heights. These tips are realized by developing and optimizing three techniques: (1) prototyping using focused-ion-beam chemical vapor deposition (FIB-CVD), electron-beam-induced deposition (EBID), and electron-beam cutting using the beam of a transmission electron microscope (TEM); (2) batch fabrication using electron-beam lithography (EBL), laser stamping, and chemical etching; and (3) an alternative method oriented to batch fabrication and a risk mitigation plan for batch fabrication called "strain engineering of pre-stress thin films."

In-situ prototyping of sub-10-nm-gap dual-tip AFM cantilevers based on metal layer coating, FIB chemical vapor deposition (FIB-CVD), EBID, and e-beam cutting inside a TEM are shown schematically in FIG. 7. The procedures are as follows:

Step 1. Starting with a commercially available AFM cantilever with pre-coated metal (gold) layer on both sides (top and bottom), FIB is used to cut the cantilever and its supporting base to form microelectrodes and lead lines with a width of about 2 µm-5 µm and 20 µm-50 µm, respectively. In case of an AFM cantilever without a metal coating, an Au layer is sputtered on both sides.

Step 2. The pyramid or cone-shaped tip may or may not have a precoated metal layer. For the former case, FIB will be used to separate the pre-coated layer into two parts, otherwise, FIB CVD will be used to directly write electrodes on the side surface with a line width of about 1 µm and a thickness of about 50-100 nm.

Step 3. The pyramid or cone-shaped tip is milled off using FIB to form two small flat surfaces with a side length of 1 µm-3 µm. As shown in FIG. 7, hollow pyramids or cones are preferred. These leave a space for the electrons to pass through as described in Step 6.

Step 4. FIBCVD or EBID are applied to grow nanotips from the flats generated in the previous step. Precursors will be Pt for FIBCVD or $CpPtMe_3$ for EBID. The growth direction will be 30° for both sides to tilt towards the inner sides. The cylindrical nanotips will have a diameter between 30-50 nm and a length of 11 µm-3 µm.

Step 5. A lateral bridge is formed on the top of cylindrical tips using the same method as Step 4.

Step 6. A focused highly energetic (200 keV to 300 keV) electron beam is then used to generate a sub-10-nm gap between the cylindrical nanotips, i.e., by cutting the bridge into two parts at the center. To achieve a sub-10-nm gap with high accuracy, a confocal scanning transmission electron microscope (CsTEM) is used. An attempt on a similar sized nanowire showed that the key to success is the control of internal stresses, which may be caused by the fabrication process in Steps 4 and 5 or the electrode bombardment in Step 6.

Other steps involving FIB and EBID have all been routinely used for 20 years by one of the present inventors and his team, [DL2002] [DL2004] [DL2007] as shown in FIG. 8, which shows images of the preliminary results of the fabrication of FIG. 7, FIGS. 8A to 8C show use by the present inventors, and other research labs in the world [MS2000] [KR2004], Step 6 is the main challenge in creating this structure. However, it has been successfully implemented using FIBCVD for the first three steps and cutting as shown in FIG. 7, along with an as-fabricated AFM cantilever with a flat tip as shown in FIG. 8D. A carbon nanotube is then bridged between the flats and cut with the e-beam of a TEM (FIG. 8F). An initial gap of 7.6 nm has been achieved, which is encouraging and shows the feasibility of the proposed Step 6. However, the gap could not be kept within 10 nm and became larger (29.4 nm) after 5 minutes. This is attributed to the internal stress caused by the assembly process and the electron beam bombardment during cutting. In order to avoid this, an annealing process is added between Steps 5 and 6. Since it is caused by the electron beam bombardment, the physics behind the expansion is complicated. To avoid charging effects, the electrodes are shortened before Step 6 or cut after Step 6 rather than in Step 3. In any cases, the feasibility and scalability of this method is not worse than the nanopore-based method [GS2010] [HS2016] [WA2018], which has been successfully marketed since 2015.

It has been noted that this prototyping process is a time consuming one and typically takes 5-7 hours for a single cantilever. To shorten the time, the bridge (Step 5) is fabricated as thin as possible. For proof of concept, justification of a new design or new parameters, or small batch fabrication, this method is an effective and efficient way to form the cantilever with simplicity and flexibility. Furthermore, FIBCVD-based electrode direct writing is also an irreplaceable process for the EBL-based method.

Figure 9:
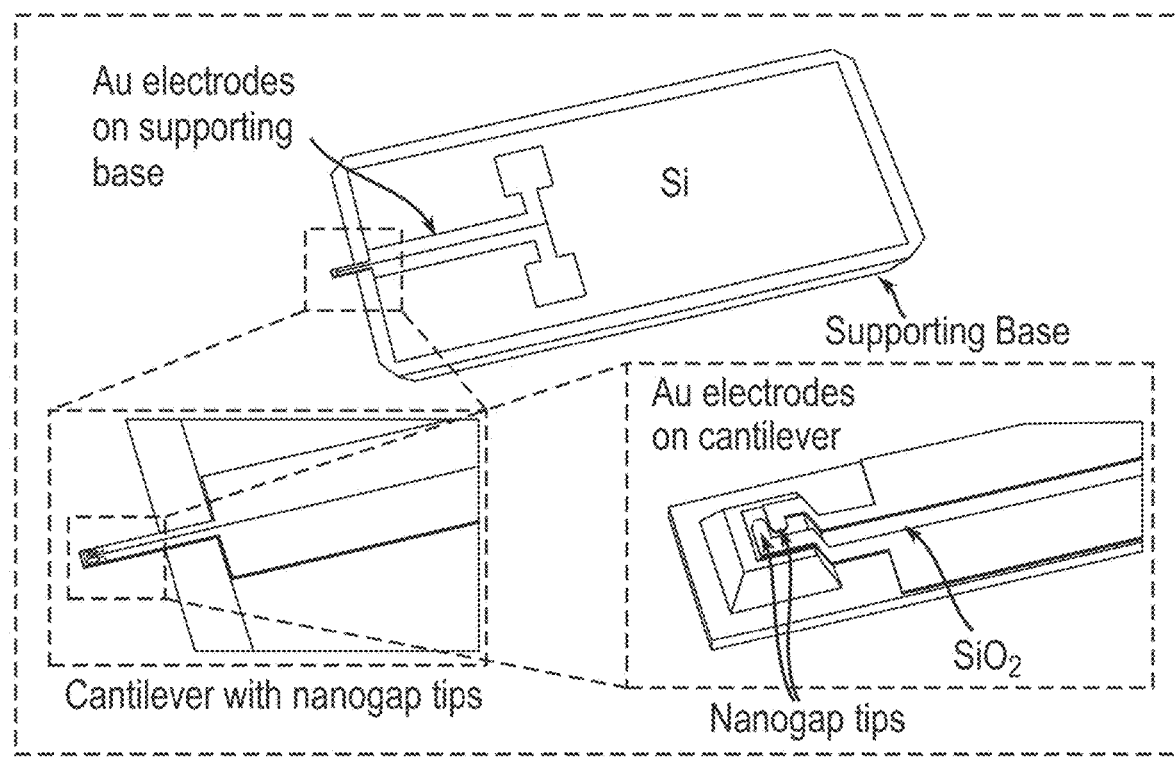
FIG. 9 is a schematic drawing of the design of sub-10-nm-gap dual-tip AFM cantilevers.
Figure 10:
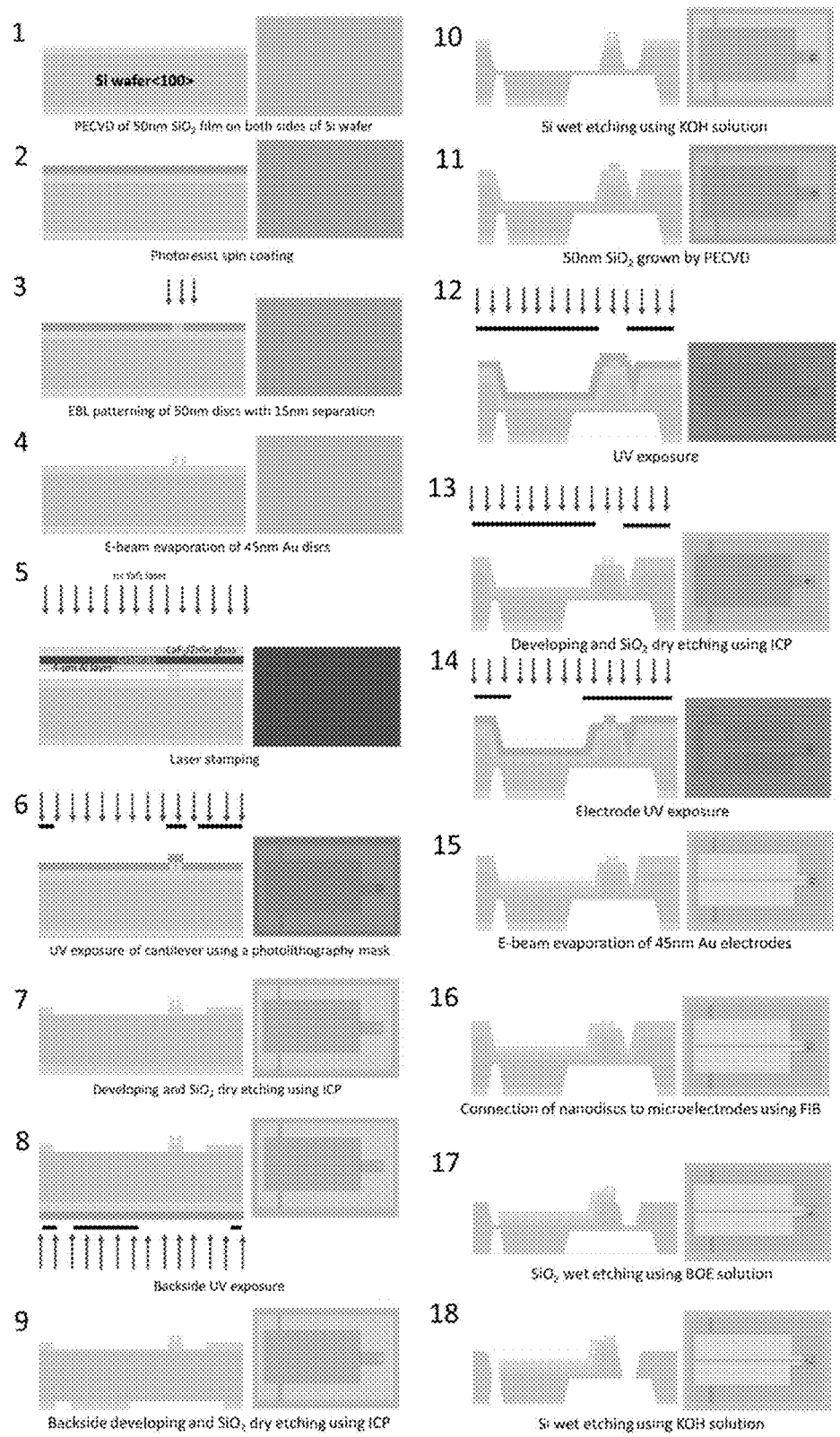
FIG. 10 illustrates the steps in a fabrication processes of sub-10-nm-gap dual-tip AFM cantilevers.

Middle scale batch fabrication of sub-10-nm-gap dual-tip AFM cantilevers can be achieved using EBL patterning and laser stamping gap shrinking. As schematically shown in FIG. 9, the design of sub-10-nm-gap dual-tip AFM cantilevers are different from regular ones in two aspects: two conductive nanotips with diameters around 50 nm and a very challenging requirement on the separation (sub 10 nm) in between. To implement it, the routinely used fabrication processes of regular AFM probes are combined with two specially designed ones: (1) the fabrication of 50-nm cylindrical tips and (2) the shrinkage of the gaps. Furthermore, the FIBCVD-based method is adapted for nanoelectrode writing. As shown in FIG. 10 the fabrication processes are as follows:

Step 1 Insulation layer preparation. Plasma-enhanced chemical vapor deposition (PECVD) is used to grow a 50-nm thick silicon dioxide ($SiO_2$) thin film. Since silicon wafers are doped semiconductors, manufacturing electrodes and antennas directly on silicon wafers may lead to a device short circuit, so an insulation layer is introduced to isolate the electrodes and conductive tips from the Si substrate. Because $SiO_2$ has good corrosion resistance, it is also used as a mask material for wet etching.

Steps 2-4 Tip fabrication. Several 50-nm cross cylindrical tips with a smallest gap around 15 nm are prepared using an EBL system to pattern the tips on a spin coated photoresist. Then e-beam evaporation of 45-nm-thick Au is used to develop the pattern.

Step 5 Tip gap shrinking using laser stamping. This is a newly designed technology (as schematically shown in FIGS. 11E and 11F) that is used for achieving smaller gaps between the cylindrical tips by pressing the as-fabricated metal discs from the top using a ns YAG laser. Three layers of materials are used for achieving this including a 4-μm-thick Al layer as compressor, a graphite one for ablative coating, and a $CaF_2$/ZeSe glass layer for transparent confinement.

Steps 6-10 Fabrication of supporting bases and cantilevers. Photolithography masks with pre-designed patterns are used together with UV exposure for both the top and bottom side patterning of the contours of a supporting base and cantilevers using spin coating of photoresist, developing and dry etching of a $SiO_2$ layer using inductively coupled plasma (ICP). Resulting windows for Si wet etching are achieved by using a KOH solution. The pyramid tips are formed after etching while the cantilevers are kept with a greater thickness than the final sizes.

Steps 11-15 Fabrication of lead out electrodes on the supporting bases and microelectrodes on the cantilevers. A 50-nm-thick layer of $SiO_2$ is grown using PECVD on the top surface as an insulating layer for the fabrication of lead out electrodes on the supporting bases and microelectrodes on the cantilevers. Then the $SiO_2$ on the top of the tips is selectively removed using dry etching with ICP based on UV exposure and developing on a spin coated photoresist layer. Then, a 45-nm-thick gold film is deposited with an e-beam evaporator, serving as electrodes.

Step 16 Connection of nanotips to the microelectrodes on cantilevers using FIBCVD. FIBCVD is used to directly write a nanoelectrode connecting the microelectrodes on cantilevers and the tips. The nanoelectrode follows a path along the pyramid side and top surfaces realizing a 3D electrical connection.

Steps 17-18 Finalization of cantilever etching. To complete the fabrication of the probe, a buffered oxide etch (BOE) is used to etch the $SiO_2$ away followed by Si etching using KOH. Note that the sacrificial layer on the front and rear sides is etched away from both the top and bottom sides, hence faster than the region with the cantilever, which will be etched from the bottom side only.

Typically, 375 probes can be patterned from a single 4" wafer with a single probe of a 3.4 mm×1.6 mm size for the supporting base and up to several hundred micrometers in length. The probes will then be tested for conductivity/insulation before using them for DNA sequencing.

One of the present inventors and his team have been working on plasmonic devices such as optical antennas for more than 10 years. This work has demonstrated spheres-on-pillar [CX2010a], match-like [CX2010b], and pentamer optical antennas and arrays of them [HC2018]. Shrinking the separation between nanostructures such as the discs shown in FIG. 11A is the key to enhance the performance of these devices. In this work an average gap of c.a. 15 nm (FIG. 11B) has been achieved using EBL-based lithography, which is also the best solution available from a commercially available apparatus. Occasionally, a sub-10-nm gap is achieved (FIG. 11C) by tilting the sample stage or using the disc pillars mutually as masks to perform shadow lithography. However, this method still lacks full controllability. Currently, a GRF project is supporting the investigation of "Plasmonic nanosensors and antennas for signal transduction and energy harvesting for biomedical microrobots" (PI: Lixin Dong, Period: 1 Jan. 2021-31 Dec. 2023). One of the objectives of the project is the design, optimization and fabrication of plasmonic detectors of molecules. FIG. 11D shows a cantilever chip with optical antennas integrated on it.

A newly developed process called "laser stamping/shocking" [GH2014] [HY2016] is used in an attempt to shrink the as-fabricated gaps between nanodisc tips. In this project, based on the metal nanodiscs with an initial gap of 15-20 nm regularly attainable from EBL and electron beam exposure, laser stamping is used to shrink the gap further to a sub-10-nm scale. Previous reported nano-discs have demonstrated the feasibility of 5-nm gaps (FIGS. 11E and 11F). In addition, laser stamping technology can achieve the gap shrinkage in a batch-fabrication fashion, which is quite compatible with the other processes for batch fabrication of AFM tips.

The key bottle neck to the scalability of the second method (i.e., EBL-based patterning, laser-stamping-based shrinkage of nanogaps, and chemical etching) is the single-beam nature of the process, i.e., either an electron beam or a focused ion beam. While the rest of the processes have comparable scalability to the mainstream technologies in the state-of-the-art semiconducting industry, energetic beam-based technologies are still facing a grand challenge commonly shared by the entire semiconductor industry. Although not very cost-effective for AFM cantilever fabrication, extreme ultraviolet lithography (EUV) has become an excellent replacement in cell phone chip manufacturing. Along with the maturity of 2-7 nm processes, EUV processes are very promising for adoption in the fabrication of AFM tips with sub-10-nm gaps.

Large scale batch fabrication of sub-10-nm-gap dual-tip AFM cantilevers using strain engineering. An alternative design for large batch fabrication is shown in FIG. 12, in which a tri-layer metal-insulator-metal (MIM) sandwich structure is patterned on a pre-stressed thin film on a substrate plane and curled-up after etching, forming a vertical tip on the end of a cantilevered beam. In this design, the thickness of the insulator layer determines the separation of the metal layers, i.e., the gap between tips.

To combine the nano-gap electrode structure with the AFM probe, the design scheme relies on the basic semiconductor fabrication processes utilizing standard ones for the AFM probe fabrication and combining them with the three-dimensional self-curling fabrication processes. The design uses the cross-section on the terminal end on the self-curling 3D structure as tips for DNA sequencing. The nano-gaps in the cross-section of the curled structure mainly rely on the atomic layer deposition (ALD) technique, which can be accurately controlled down to a sub-nanometer scale. In addition, this design scheme fully considers the compatibility with the established AFM probe fabrication process, and therefore, reliable batch production can be achieved.

Figure 13:
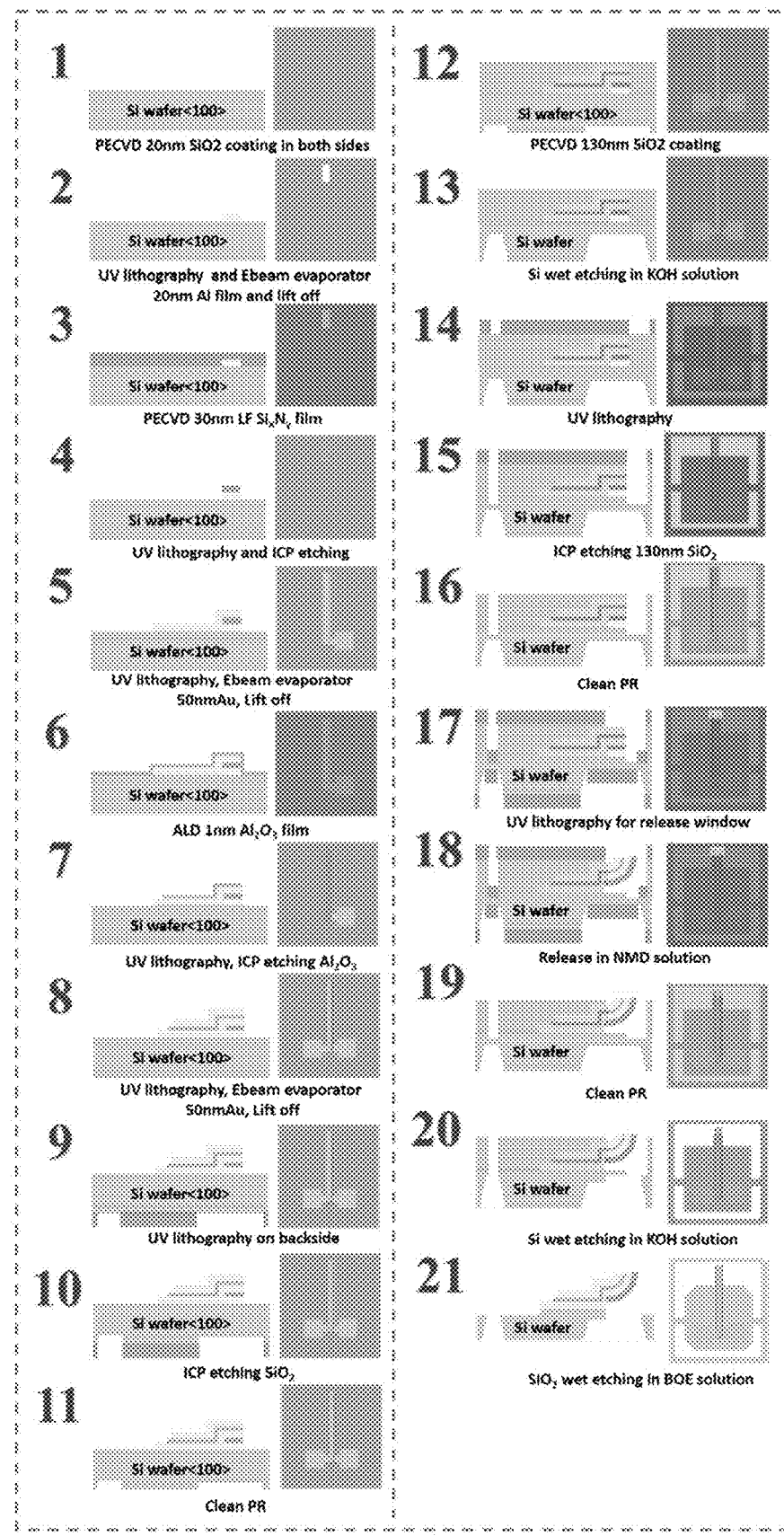
FIG. 13 shows a series of steps in a fabrication processes of sub-10-nm-gap dual-tip AFM cantilevers based on strain engineering.

The fabrication processes of this method (FIG. 13) are as follows:

Step 1 Insulation layer vapor deposition. $SiO_2$ vapor deposition is performed on both sides of Si wafers using PECVD.

Step 2 Evaporation of sacrificial layer for self-curling mesa. A 20-nm-thick Al film layer is used as sacrificial material. The Al layer deposited and then is patterned with UV exposure. The patterned film is evaporated with an electron beam and followed with a lift off process.

Steps 3 and 4 Evaporation and patterning of self-curling mesa layer. The self-curling layer is a $Si_xN_y$ film with intrinsic stress obtained from PECVD. The thickness is 30 nm. A UV lithography process is then used to design the exposure mask, and ICP etching technology is used to achieve mesa fabrication.

Step 5 Bottom electrode fabrication. A 50-nm-thick Au bottom electrode is patterned with UV exposure and formed with electron-beam evaporation.

Step 6 Evaporation of nano-gap insulating layer. A 1-mm $Al_2O_3$ film is obtained using ALD deposition technology.

Step 7 Nano-gap insulating layer patterning. Using photoresist as a mask, ICP etching is used to retain the $Al_2O_3$ film above the bottom electrode.

Step 8 Top electrode fabrication. UV exposure is used for top electrode patterning, and electron beam vapor deposition and lift off techniques are used to obtain a 50 nm Au film.

Step 9 Backside UV Lithography

Step 9 Backside UV lithography. In order to pre-etch the backside Si, it is necessary to use photoresist to create etching window patterns, so the back-jacketing method is used to obtain etching window patterns.

Step 10 Etching window fabrication. ICP etching of $SiO_2$ is used to make the etching material Si exposed.

Step 11 Removal of photoresist. Acetone is used to remove the etching window photoresist.

Step 12 Anti-corrosion protective layer vapor deposition. Since KOH solution can also be used as an etchant for the sacrificial layer Al in the self-curling structure, it is necessary to vaporize the anti-etching protection layer on the substrate surface. PECVD is used to vaporize a 130 nm $SiO_2$ protection layer.

Step 13 Bottom Si substrate etching. The substrate is placed in a KOH solution at room temperature for the etching of the substrate Si. Since the thickness of the micro-cantilever needs to be ensured, the time of KOH solution etching needs to be strictly controlled to ensure sufficient thickness of the cantilever beam Si substrate.

Steps 14-15 UV exposure and etching of the top etching window. To transfer the etching window pattern to the top of the substrate, UV lithography is used together with ICP to etch the 130 nm $SiO_2$ protective layer.

Step 16 Removal of Photoresist

Step 16 Removal of photoresist. Acetone is used to remove the etched window photoresist.

Step 17 Self-curling release window patterning. UV exposure is used to obtain the self-curling release window pattern.

Step 18 Self-curling structure release. NMD solution is used to etch the sacrificial layer Al to gradually release the curling structure.

Step 19 Photoresist removal. The sample with its self-curling structure is placed in acetone solution to remove the photoresist.

Step 20 Si etching. KOH is used to etch the silicon substrate. Only the Si at the point where the upper and lower release windows are connected can be etched away.

Step 21 Removal of the protective layer of $SiO_2$. The sample is placed in the BOE etching solution to completely etch the exposed $SiO_2$ and then it is placed in aqueous solution to rest to obtain an AFM probe with a self-curling structure.

Based on strain engineering, 3D structures can be created through a pre-strained 2D nanometer thick heteroepitaxial bilayer due to curling up (FIG. 14A) based on a pair of opposing forces ($F_1$ and $F_2$) that form 3D structures [PV2000]. The present inventors have successfully demonstrated the controllable fabrication and characterization of a variety of rolled-up 3D helical nanostructures with nanoscale features such as SiGe/Si tubes (FIG. 14B), diameters between 10 nm and 10 μm), Si/Cr rings (FIG. 14C), [ZL2008], see Ref. [SO2005] for InGaAs/metal structures), SiGe/Si coils [ZL2005] (FIG. 14D), InGaAs/GaAs coils [BD2006] (FIG. 14E), small-pitch InGaAs/GaAs coils (FIG. 14F), Si/Cr claws (FIG. 14G), Si/Cr spirals [ZL2006a] (FIG. 14H), and small-pitch SiGe/Si/Cr coils [ZL2006b] (FIG. 14I). The present inventors developed special processes such as rolling/unrolling and winding/unwinding for the manipulation of various rolled-up 3D helical nanostructures such as SiGe/Si and InGaAs/GaAs tubes [BD2006], coils, rings and spirals and the smallest robotic swimmers from pre-stressed bilayers such as SiGe/Si and InGaAs/GaAs for locomotion at the low Reynold's number region, and many other nanosystems [DL2006] [DL2009].

Currently, a GRF project (11219419) is supporting the investigation of "Memoristic ambient oxygen nanosensors for medical microrobotic agents" (PI: Lixin Dong, Period: 1 Oct. 2019-30 Sep. 2022), with one of the objectives being the stress-engineering of microrobotic agents with nanoelectrodes. Half curled up structures have two stable states including the horizontal one and the curled up one as shown in FIGS. 14J and 14K, making it possible for such structures to serve as a cantilever. This method makes it possible to omit FIB-based electrode writing. The idea to transform the gaps between cantilever tips into the thickness of insulator layer has a remarkable commercialization value. Theoretically speaking, it is possible to implement a sub-one-nm gap based on ALD or using 2D materials.

Machine learning method for iterative DNA sequencing. While the end-effector of the nano robot is moving along a DNA strand, the electrical signals are measured. Since the highest occupied molecular orbital (HOMO) energy for the four kinds of DNA nucleobases are as follows: G (−5.7 eV)>A (−5.9 eV)>C (−6.1 eV)>T (−6.6 eV) [TO2012], the difference between these HOMO energy values constitutes the basis of DNA sequencing with the nano robot. Specifically, two electrodes on the end-effector can measure the HOMO energy of nucleobases. Theoretically, if the electrodes are small enough and the interval between the electrodes is equal to the size of the nucleobase, by moving the end-effector, each nucleobase can be measured independently. However, based on the state-of-the-art fabrication technology, the minimal distance between the electrodes will be larger than a nucleobase. For instance, each electrode is 50 nm and there is a 5 nm space in between as shown in FIG. 15. The size of each nucleobase is about 0.5 nm, so the interval between the two electrodes spans about 10 nucleobases and each electrode will cover about 100 nucleobases. Therefore, the practical measurement scenario will be that shown in FIG. 16.

The essence of HOMO energy is electrical potential energy, so for a single DNA chain, it can be regarded as a chain of batteries with different voltages. Those batteries covered by the electrodes can be viewed as being short-circuited, as shown in FIG. 17. Therefore, the electric potential difference between the two electrodes will be the sum of the 10 nucleobases between the two electrodes. Based on this insight, the physical size of the electrodes can be neglected and the contact between the electrodes and the DNA chain can be taken as point contact, with no influence on the ultimate measurement results, as shown in FIG. 18.

Because one measurement value is a sum of 10 nucleobases, those nucleobases in the middle of the DNA chain can exert their influence on 10 measurement values, but those at the beginning and end of the DNA chain are measured much less. In order to balance this unfairness, nine known nucleobases are connected to both the beginning and end of the DNA chain. Since the HOMO energy of the T nucleobase is the most distinguishable, the known nucleobase is chosen to be T. This concatenation operation is illustrated in FIG. 19.

Assume the total number of nucleobases after concatenation of T at the beginning and end of the DNA chain is n, there will be n-9 measurements to be conducted in one measurement loop. The noise-free measurements should conform to the equations shown in FIG. 20, where x represents the HOMO energy values of each nucleobase and b represents the measurement values without noise. The first 18 equations indicate the known ground truth about the connected T nucleobases.

Under practical circumstance of measurement, there will inevitably be noise. For the DNA sequence measurement case, there will be two kinds of noise. The first noise is the contact noise between the electrodes and DNA strand or chain, which can be approximated by Gaussian noise added to the measurement values. The second noise comes from nano robot end-effector motion error, which is modelled with beta noise, as shown in FIG. 21. The electrodes may not be exactly moved to the junction of two adjacent nucleobases, but with some deviation δ. The deviation is assumed not to exceed the length of one nucleobase. The probability distribution for different deviation values is approximated with beta distribution $$\delta \sim \frac{1}{2B(\alpha, \alpha)}\left(\frac{x+1}{2}\right)^{\alpha-1}\left(\frac{1-x}{2}\right)^{\alpha-1}.$$

Due to the elasticity of the DNA chain, the deviation for the two electrodes may not be the same. Two independent random variables $\delta_1$ and $\delta_2$ are allocated to each electrode. This deviation will directly affect the measurement matrix. The actual measurement matrix will not be the one in FIG. 20 anymore, but becomes the one shown in FIG. 22. However, the beta noise value is unknown, so when solving the DNA sequence, the measurement matrix used is still the one in FIG. 20. But the measurement values are affected by both Gaussian noise and beta noise, as shown in FIG. 23.

The equation in FIG. 23 is an overdetermined equation, which can be solved by a neural network. The neural network structure that is used is shown in FIG. 24. The inputs to the neural network are the position serials of each nucleobase, such as 1, 2, 3 . . . , while the outputs of the network are the HOMO energy values of the nucleobases at the corresponding positions. If the equation is abbreviated as Ax=d, the loss function for training the neural network is defined as L=‖Ax−d‖$_2^2$. By minimizing the loss value, the best DNA sequence can be solved.

Due to the existence of noise, one loop of measurement is not enough to acquire a convincing DNA sequence. Multiple measurements are necessary. It is easy to scale up the measurement equation in FIG. 23. New measurements can be directly added at its end as new rows. Once a new loop of measurement is finished, a new result about the DNA sequence can be calculated. In order to improve efficiency, the training result after the last measurement is used as the initialization of the next calculation. In this manner, a new candidate of the DNA sequence will be generated after each new loop of measurement. With the increase of measurement times, the difference between the generated DNA sequence will become smaller and smaller, until it does not change anymore. The difference between two adjacent results can be used to calculate the confidence interval of the generated DNA sequence. This iterative DNA sequencing framework is illustrated in FIG. 25.

Simulation studies were conducted to test the DNA sequencing framework under both Gaussian contact noise and beta motion error. The first 30 nucleobases of the DNA sequence of a green fluorescent protein were used as the ground truth, which are "TTACCAATGCTTAATCAGT-GAGGCACCTAT (SEQ ID NO: 1)." First, only Gaussian contact noise was used to corrupt the measurement values, with the used Gaussian noise e~N(0, 0.04). The average DNA sequencing accuracy with respect to measurement times is shown in FIG. 26. Second, only beta motion error of the nano robot end effector motion was considered, with the beta error equal to $$\delta \sim \frac{1}{2B(1000, 1000)}\left(\frac{x+1}{2}\right)^{999}\left(\frac{1-x}{2}\right)^{999}.$$

The average DNA sequencing accuracy with respect to measurement times is shown in FIG. 27. Finally, both the Gaussian contact noise and beta motion error are considered, which are the same as those used in the first and second simulations. The simulation result is shown in FIG. 28. For all cases, the accuracy increases with an increase in the number of measurement times, which proves the effectiveness of the DNA sequencing framework of the present invention. More importantly, it demonstrates the significance of using multiple measurements to improve the accuracy of sequencing.

The above simulation results are based on ideal models of contact noise and motion error. In reality, the contact noise may not exactly conform to a Gaussian distribution and the motion error also may not exactly conform to a beta distribution. The Gaussian model and beta model can only be used as a very good reference. The real distributions of noises must be calibrated. For this purpose, the present invention uses a machine learning based calibration method as follows: Measurements are conducted on several pre-known DNA sequences so that noise values can be separated. In this way, some data about noises can be obtained, although very limited. Then a new calibration framework based on the newly developed Generative Adversarial Tri-model (GAT model) [SW2020] can be used to calibrate the noise distribution. The GAT model can take advantage of the approximate qualitative model to facilitate machine learning so as to reduce the training data demand.

The basic idea of the GAT model is shown in FIG. 29. Explicitly, there are two kinds of model in it, i.e., a machine learning model and an analytical model. The specific machine learning model can be any kind of supervised learning model or unsupervised learning model, not just restricted to a neural network. These machine learning models can be trained independently until convergence with labelled or unlabelled data, or even without data. The analytical model may depend on any kind of knowledge about the machine learning outputs, like physical knowledge or mathematical knowledge. Therefore, the analytical models can be used to correct the imperfect outputs of machine learning models. Next, the machine learning models will be re-initialized based on the corrected outputs and trained again until convergence from this new initialization. The whole process forms a loop and will converge when the machine learning outputs conform to the analytical models to some acceptable degree or vice versa.

A machine learning model is usually used to represent some complex functional relationship, such as the noise distributions in the present DNA sequencing problem. The distributions are expected to be obtained through training on data. But the training data could be difficult to get, so there may be only a small amount of data, or data with biases. There are many reasons that the machine learning results are imperfect or do not conform to some necessary constraint. However, if some extra knowledge is known about the desired functions, this knowledge can be used to adjust the temporal machine learning outputs. As a result, the machine learning models are re-initialized based on adjusted outputs and undergo further training again. In the GAT model of the present invention, the functional relationship is generated by the machine learning model, so it acts as a generator. The machine learning model and analytical model optimize this function in turn in an adversarial way. The two kinds of models are in competition because the analytical model wants the function to conform more to the extra knowledge, while the machine learning model wants the function to conform more to the loss function in terms of smaller loss values. But this competition is a positive-sum rather than a zero-sum like most Generative-Adversarial-Network (GAN) [CA2018] because this functional relationship is expected to conform to both loss function and extra knowledge.

The most vital conjunction point in the GAT model is how to re-initialize the machine learning model with adjusted outputs. A feasible approach has been developed with respect to the neural network shown in FIG. 24. This fully-connected network with just one hidden layer is able to reproduce any function, so it can be used to generate the required noise distribution. The reproduction procedure is illustrated in FIG. 30. For an arbitrary function (indicated by the blue curve), a series of points $(0, y_0), (x_1, y_1), (x_2, y_2)$ and $(x_3, y_3)$ can be sampled from it. The original function can be approximated by a piecewise linear function consisting of the line segments connecting every two adjacent points. The prolongations of these line segments are represented by $l_1$, $l_2$ and $l_3$. For the specific case on the right of FIG. 30, the piecewise linear function can be expressed by $l_1+\text{ReLU}(l_2-l_1)-\text{ReLU}(l_2-l_3)$, which naturally conforms to the functional relationship represented by the neural network.

For the general case, if the sampled data points are $(x_0, y_0), (x_1, y_1), \ldots, (x_n, y_m)$, a formulaic algorithm has been developed to initialize every parameter in the neural network so that the neural network can reproduce the piecewise linear function connecting these sampled points. This algorithm is described with pseudocode as follows, where $\text{sgn}(\cdot)$ is the sign function.

Algorithm 1:

$$w_1^{[1]} \leftarrow \left|\frac{y_1 - y_0}{x_1 - x_0}\right|$$

$$b_1^{[1]} \leftarrow -w_1^{[1]} \cdot x_0$$

$$w_1^{[2]} \leftarrow \text{sgn}\left(\frac{y_1 - y_0}{x_1 - x_0}\right)$$

for i from 2 to n $$w_i^{[1]} \leftarrow \left|\frac{y_i - y_{i-1}}{x_i - x_{i-1}} - \frac{y_{i-1} - y_{i-2}}{x_{i-1} - x_{i-2}}\right|$$

$$b_i^{[1]} \leftarrow -w_i^{[1]} \cdot x_{i-1}$$

$$w_i^{[2]} \leftarrow \text{sgn}\left(\frac{y_i - y_{i-1}}{x_i - x_{i-1}} - \frac{y_{i-1} - y_{i-2}}{x_{i-1} - x_{i-2}}\right)$$

end
$$b^{[2]} \leftarrow y_0$$

With Algorithm 1, the adjusted outputs by the analytical model can be used to re-initialize the neural network so that the network can refine the adjusted outputs with further training. With the alternation between machine learning model and analytical model, the GAT model outputs are also evolving. Several indexes about the GAT model outputs can be defined to indicate the properties of outputs at different stages. These indexes can be combined to form different states. Then the running of the GAT model can be viewed from another perspective of state transition, such as a Discrete Event Dynamic System (DEDS) model. Therefore, the convergence as well as the stability of the GAT model can be analyzed.

The specific GAT model application in noise calibration is illustrated in FIG. 31. In the GAT model, the neural network is used as a generator to generate the probability distributions of the noise. The input of the network is different noise values and the output is its corresponding probability density value. The network is first trained on experimental noise data from random initialization until convergence. Then the generated distribution is used to quantify the unknown constants in both the Gaussian model and beta model, as well as their fusion weight. The quantified noise models are then used to re-initialize the neural network with Algorithm 1. Then the network is trained again on experiment data. The whole GAT model converges when the loss value is smaller than some threshold E. In this way, the distribution that the real measurement noise conforms to can be calibrated. Based on the noise levels, the required measurement times for certain confidence of sequencing, for instance, 99% can be estimated.

In summary, the proposed nano robotic system will enable repeat measurements of a DNA strand and system calibrations before sequencing. These key capabilities provide the foundation for applying the proposed GAT model-based machine learning method to analyse the sequencing data and estimate the confidence of the obtained sequences. As a result, it will significantly improve the accuracy and reliability of the sequencing results.

Experimental testing and verification of the nano robotic system of the present invention was divided into two phases. Phase I concentrated on evaluating the system in terms of the technical competency such as accuracy of the sequencing, sequencing speed, and robustness of the software. Phase II concentrated on comparative studies to compare the performance of the system with market available sequencing methods and systems such as BotSeqS, NanoSeq and ION.

The following sample preparation protocol was used to set up a single DNA strand for sequencing:
  Isolate target single cells by mechanical dissociation and/or enzymatic digestion
  Extract genomic DNA
  Remove any residual RNA like lncRNA and miRNA, and proteins like histones
  Generate linear single-stranded DNA and prevent the reforming of base pairs
  Connect both ends with known strands so as to tag them with identifiable barcodes
  Straighten and fix the single strand on a flat substrate and keep all bases in same orientation.

In the first step, known DNA sequences are used to calibrate and verify the system. Later, unknown sequences will be sequenced. At the same time, they will also be sequenced using other techniques to verify the results.

In addition, the following studies were used for the Phase II studies:
  Human EPSCs can first undergo random genomic mutation by gamma or ultra-violet irradiation. Alternatively, they can be subjected to precise genome editing by CRISPR-Cas9 mediated knockout or knock in. Single cell DNA libraries can be prepared and undergo PCR-based, nanopore-based, and nano robot-based in a side-by-side manner to showcase the efficiency and demonstrate the accuracy of the nano robot-based system.
  Cancer cell lines and primary tumors can be expanded in vitro and subjected to nano robot-based genomic DNA sequencing to demonstrate superior efficiency and accuracy over other sequencing methods. The DNA sequences can be used to infer cell lineages and trace back to cancer stem cell populations.

The current market for third generation sequencing is dominated by ION made by Oxford Nanopore, a UK based company. The ION system is based on biological nanopore. While single strand DNA in a fluid passes the nanopore, the ionic current between the inside and outside of a chamber changes due to the DNA blockage of the nanopore. The ionic current can be measured and provides the information on the sequence of the DNA strand.

The major technological difference between the present invention and the ION system is that with the present invention the measured DNA strand is fixed on a substrate and the measuring electrodes are moved instead of moving a DNA strand so it goes through a fixed nanohole with an electrode. This technological difference overcomes the major difficulties and disadvantages faced by the ION system, such as no control of DNA moving speed, measurement in a liquid environment, as well as missing bases. It is obvious that moving a nano robot end-effector is much easier to control than moving a DNA strand. More importantly, a DNA strand can only pass a nanopore once in the ION system and the measurement cannot be repeated. However, the nano robot end-effector of the present invention can move back and forth repeatedly on a fix DNA strand. This allows for the application of advanced data analytics, such as machine learning, to significantly improve the measurement accuracy.

Furthermore, the ION system has huge problems in sequencing DNA strands with the same bases. The same bases don't cause any changes in ionic current while passing through the nanopore since the DNA blockages in the nanopore are same. As a result, the sequencing has a lower accuracy in short-read sequencing and is not optimal for single nucleotide variation (SNV) [NK2019][SA2020]. The main reason is that ION can only use the changes of the ionic current to detect bases without knowing the position of the bases, nor whether a base has passed the nanopore. In direct contrast, the nano robot of the present invention can not only make the measurements repeatedly, but it can also register the positions of the bases while making the measurement. This advantage easily solves the problem that ION faces.

In addition, the microfluid cells used in ION are one-time use only. Beside increasing the cost of sequencing, more critically it makes it impossible to calibrate the device before using it. This could significantly increase the error of sequencing. However, the present invention has no consumable parts. The nano robot end-effector can be used multiple times and can be carefully calibrated in advance. Therefore, the cost of sequencing is much less and the sequencing error can be significantly reduced.

REFERENCES

The cited references in this application are incorporated herein by reference in their entirety and are as follows:

[BD2006] D. J. Bell, L. X. Dong, B. J. Nelson, M. Golling, L. Zhang, and D. Grutzmacher, "Fabrication and characterization of three-dimensional InGaAs/GaAs nanosprings," Nano Letters, vol. 6, no. 4, pp. 725-729, April 2006.

[BG1986] Binnig, G., C. F. Quate, and C. Gerber, "Atomic force microscope," Physical Review Letters, Vol. 56, p. 930, (1986).

[CA2018] A. Creswell, T. White, V. Dumoulin, K. Arulkumaran, B. Sengupta, and A. A. Bharath, "Generative adversarial networks: An overview," IEEE Signal Processing Magazine, vol. 35, no. 1, pp. 53-65, 2018.

[CD2010b] X. D. Cui, W. H. Zhang, D. Erni, and L. X. Dong, "Optical properties of a nanomatch-like plasmonic structure," Journal of the Optical Society of America a-Optics Image Science and Vision, vol. 27, no. 8, pp. 1783-1790, August 2010.

[CG2016] C. G. Brown, and J. Clarke, "Nanopore development at Oxford nanopore," Nature biotechnology, vol. 34, no. 8, pp. 810-811, 2016.

[CH2010] Chen, H., N. Xi, K. W. Lai, C. K. Fung, and R. Yang, "Development of infrared detectors using single carbon-nanotube-based field-effect transistors," IEEE transactions on nanotechnology, Vol. 9, pp. 582-589, (2010).

[CX2010a] X. Cui, L. X. Dong, W. Zhang, W. Wu, Y. Tang, and D. Erni, "Numerical investigations of a multi-walled carbon nanotube-based multi-segmented optical antenna," Applied Physics B-Lasers and Optics, vol. 101, no. 3, pp. 601-609, November 2010.

[DB2020] https://www.pharmiweb.com/press-release/2020-11-23/dna-sequencing-next-generation-sequencing-market-2020-forecast-with-top-companies-growth-factors.

[DL2002] L. X. Dong, F. Arai, and T. Fukuda, "Electron-beam-induced deposition with carbon nanotube emitters," Applied Physics Letters, vol. 81, no. 10, pp. 1919-1921, September 2002.

[DL2004] L. X. Dong, F. Arai, and T. Fukuda, "Destructive constructions of nanostructures with carbon nanotubes through nanorobotic manipulation," IEEE/ASME Transactions on Mechatronics, vol. 9, no. 2, pp. 350-357, June 2004.

[DL2006] L. X. Dong, B. J. Nelson, T. Fukuda, and F. Arai, "Towards Nanotube Linear Servomotors," IEEE Transactions on Automation Science and Engineering, vol. 3, no. 3, pp. 228-235, July 2006.

[DL2007a] L. X. Dong, A. Subramanian, and B. J. Nelson, "Carbon nanotubes for nanorobotics," Nano Today, vol. 2, no. 6, pp. 12-21, December 2007.

[DL2007b] Dong, L., L. Zhang, D. J. Bell, D. Grutzmacher, and B. J. Nelson, "Nanorobotics for creating NEMS from 3D helical nanostructures," in Journal of Physics: Conference Series, p. 257, (2007).

[DL2009] L. X. Dong, L. Zhang, B. E. Kratochvil, K. Y. Shou, and B. J. Nelson, "Dual-Chirality Helical Nanobelts: Linear-to-Rotary Motion Converters for Three-Dimensional Microscopy," Journal of Microelectromechanical Systems, vol. 18, no. 5, pp. 1047-1053, October 2009.

[FA2021] F. Abascal, L. M. Harvey, E. Mitchell, A. R. Lawson, S. V. Lensing, P. Ellis, A. J. Russell, R. E. Alcantara, A. Baez-Ortega, and Y. Wang, "Somatic mutation landscapes at single-molecule resolution," Nature, pp. 1-6, 2021.

[FC2009] Fung, C. K. M., N. Xi, B. Shanker, and K. W. C. Lai, "Nanoresonant signal boosters for carbon nanotube based infrared detectors," Nanotechnology, Vol. 20, p. 185201, (2009).

[FT2013] F. Traversi, C. Raillon, S. Benameur, K. Liu, S. Khlybov, M. Tosun, D. Krasnozhon, A. Kis, and A. Radenovic, "Detecting the translocation of DNA through a nanopore using graphene nanoribbons," Nature nanotechnology, vol. 8, no. 12, pp. 939-945, 2013.

[GC2019] Gawad C. et. al Single-cell genome sequencing: current state of the science. Nat Rev Genet. 2016 March; 17(3):175-88.

[GH2014] H. Gao, Y. W. Hu, Y. Xuan, J. Li, Y. L. Yang, R. V. Martinez, C. Y. Li, J. Luo, M. H. Qi, and G. J. Cheng, "Large-scale nanoshaping of ultrasmooth 3D crystalline metallic structures," Science, vol. 346, no. 6215, pp. 1352-1356, December 2014.

[GM2017] https://www.statista.com/statistics/940953/oxford-nanopore-sales-by-geographical-market-united-kingdom-uk/

[GS2010] S. Garaj, W. Hubbard, A. Reina, J. Kong, D. Branton, and J. A. Golovchenko, "Graphene as a subnanometre trans-electrode membrane," Nature, vol. 467, no. 7312, pp. 190-193, September 2010.

[GV2020] https://www.grandviewresearch.com/press-release/global-single-cell-genome-sequencing-market.

[GX2019] Gao X. et. Al. Establishment of porcine and human expanded potential stem cells. Nat Cell Biol. 2019 June; 21(6):687-699.

[HC2018] C. Hou, Y. Wang, L. Yang, B. Li, Z. Cao, Q. Zhang, Y. Wang, Z. Yang, and L. Dong, "Position sensitivity of optical nano-antenna arrays on optoelectronic devices," Nano Energy, vol. 53, pp. 734-744, 2018.

[HP2010] Harris, P. V., D. Welner, K. McFarland, E. Re, J.-C. Navarro Poulsen, K. Brown, R. Salbo, H. Ding, E. Vlasenko, and S. Merino, "Stimulation of lignocellulosic biomass hydrolysis by proteins of glycoside hydrolase family 61: structure and function of a large, enigmatic family," Biochemistry, Vol. 49, pp. 3305-3316, (2010).

[HS2016] S. J. Heerema and C. Dekker, "Graphene nanodevices for DNA sequencing," Nature Nanotechnology, vol. 11, no. 2, pp. 127-136, February 2016.

[HY2016] Y. W. Hu, Y. Xuan, X. L. Wang, B. W. Deng, M. Saei, S. Y. Jin, J. Irudayaraj, and G. J. Cheng, "Superplastic Formation of Metal Nanostructure Arrays with Ultrafine Gaps," Advanced Materials, vol. 28, no. 41, pp. 9152-9162, November 2016.

[IS2013] Ido, S., K. Kimura, N. Oyabu, K. Kobayashi, M. Tsukada, K. Matsushige, and H. Yamada, "Beyond the helix pitch: direct visualization of native DNA in aqueous solution," ACS nano, Vol. 7, pp. 1817-1822, (2013).

[JL2001] J. Li, D. Stein, C. McMullan, D. Branton, M. J. Aziz, and J. A. Golovchenko, "Ion-beam sculpting at nanometre length scales," Nature, vol. 412, no. 6843, pp. 166-169, 2001.

[JS2017] J. Shendure, S. Balasubramanian, G. M. Church, W. Gilbert, J. Rogers, J. A. Schloss, and R. H. Waterston, "DNA sequencing at 40: past, present and future," Nature, vol. 550, no. 7676, pp. 345-353, 2017.

[KR2004] R. Kometani, T. Morita, K. Watanabe, T. Hoshino, K. Kondo, K. Kanda, Y. Haruyama, T. Kaito, J. I. Fujita, M. Ishida, Y. Ochiai, and S. Matsui, "Nanomanipulator and actuator fabrication on glass capillary by focused-ion-beam-chemical vapor deposition," Journal of Vacuum Science & Technology B, vol. 22, no. 1, pp. 257-263, January-February 2004.

[LA2015] L. A. E. Leal, and O. Lopez-Acevedo, "On the interaction between gold and silver metal atoms and DNA/RNA nucleobases—a comprehensive computational study of ground state properties," Nanotechnology Reviews, vol. 4, no. 2, pp. 173-191, 2015.

[LC2017] C Li, Y Cheng, S Bi, Y Cal, N Xi, learning object recognition based on compressive sampling, 2017 IEEE International Conference on Robotics and Biomimetics (ROBIO), Macau, China, 5-8 Dec. 2017.

[LC2018] C Li, Y Cheng, Z Sun, P He, S Bi, N Xi, Content-Based Compressive Sensing, 2018 IEEE 8th Annual International Conference on CYBER Technology in Automation, Control, and Intelligent Systems (CYBER), Tianjin, China, 19-23 Jul. 2018.

[LC2020] Lareau, C. A., Ma, S., Duarte, F. M. & Buenrostro, J. D. Inference and effects of barcode multiplets in droplet-based single-cell assays. Nat. Commun. 11, 866 (2020).

[LG2014] Gongxin Li, Peng Li, Yuechao Wang, Wenxue Wang, Ning Xi, Lianqing Liu, "Efficient Imaging and Real-Time Display of Scanning Ion Conductance Microscopy Based on Block Compressive Sensing", International Journal of Optomechatronics January 2014; 8(3).

[LG2015] Gongxin Li; Wenxue Wang; Yuechao Wang; Shuai Yuan; Wenguang Yang; Ning Xi; Lianqing Liu, "Nano-Manipulation Based on Real-Time Compressive Tracking" IEEE Transactions on Nanotechnology, Volume: 14, Issue: 5, September 2015

[LK2009a] Lai, K. W. C., N. Xi, C. K. M. Fung, H. Chen, and T.-J. Tarn, "Engineering the band gap of carbon nanotube for infrared sensors," Applied Physics Letters, Vol. 95, p. 221107, (2009).

[LK2009b] Lai, K. W. C., N. Xi, C. K. M. Fung, J. Zhang, H. Chen, Y. Luo, and U. C. Wejinya, "Automated nano-manufacturing system to assemble carbon nanotube based devices," The International Journal of Robotics Research, Vol. 28, pp. 523-536, (2009).

[LL2002] Lynd, L. R., P. J. Weimer, W. H. Van Zyl, and I. S. Pretorius, "Microbial cellulose utilization: fundamentals and biotechnology," Microbiol. Mol. Biol. Rev., Vol. 66, pp. 506-577, (2002).

[LY2011] Liu, Y.-S., J. O. Baker, Y. Zeng, M. E. Himmel, T. Haas, and S.-Y. Ding, "Cellobiohydrolase hydrolyzes crystalline cellulose on hydrophobic faces," Journal of Biological Chemistry, Vol. 286, pp. 11195-11201, (2011).

[ML2016] M. L. Hoang, I. Kinde, C. Tomasetti, K. W. McMahon, T. A. Rosenquist, A. P. Grollman, K. W. Kinzler, B. Vogelstein, and N. Papadopoulos, "Genome-wide quantification of rare somatic mutations in normal human tissues using massively parallel sequencing," Proceedings of the National Academy of Sciences, vol. 113, no. 35, pp. 9846-9851, 2016.

[MS2000] S. Matsui, T. Kaito, J. Fujita, M. Komuro, K. Kanda, and Y. Haruyama, "Three-dimensional nanostructure fabrication by focused-ion-beam chemical vapor deposition," Journal of Vacuum Science & Technology B, vol. 18, no. 6, pp. 3181-3184, November-December 2000.

[MT2019] M. T. Noakes, H. Brinkerhoff, A. H. Laszlo, I. M. Derrington, K. W. Langford, J. W. Mount, J. L. Bowman, K. S. Baker, K. M. Doering, and B. I. Tickman, "Increasing the accuracy of nanopore DNA sequencing using a time-varying cross membrane voltage," Nature biotechnology, vol. 37, no. 6, pp. 651-656, 2019.

[NK2019] Kono N, Arakawa K. Nanopore sequencing: Review of potential applications in functional genomics. Dev Growth Differ. 2019 June; 61(5):316-326.

[NN2018] Nikooienejad, N., A. Alipour, M. Maroufi, and S. R. Moheimani, "Video-Rate Non-Raster AFM Imaging With Cycloid Trajectory," IEEE Transactions on Control Systems Technology, 2018).

[NT2015] https://www.nature.com/articles/nrg.2015.16.

[PP2018] P. Pungetmongkol, "Speculation of Nano-gap Sensor for DNA sequencing technology: A Review on Synthetic Nanopores," Engineering Journal, vol. 22, no. 6, pp. 229-250, 2018.

[PS2020] https://www.prnewswire.com/news-releases/next-generation-sequencing-data-analysis-market-size-worth-1-72-billion-by-2028-grand-view-research-inc-301229618.html

[PV2000] V. Y. Prinz, V. A. Seleznev, A. K. Gutakovsky, A. V. Chehovskiy, V. V. Preobrazhenskii, M. A. Putyato, and T. A. Gavrilova, "Free-standing and overgrown InGaAs/GaAs nanotubes, nanohelices and their arrays," Physica E, vol. 6, no. 1-4, pp. 828-831, February 2000.

[RR2019] R. R. Wick, L. M. Judd, and K. E. Holt, "Performance of neural network basecalling tools for Oxford Nanopore sequencing," Genome biology, vol. 20, no. 1, pp. 1-10, 2019.

[SA2020] Amarasinghe S L, Su S, Dong X, Zappia L, Ritchie M E, Gouil Q. Opportunities and challenges in long-read sequencing data analysis. Genome Biol. 2020 Feb. 7; 21(1):30.

[SB2014] B. Song, J. Zhao, N. Xi, H. Chen, K. W. C. Lai, R. Yang, L. Chen, "Compressive Feedback-Based Motion Control for Nanomanipulation—Theory and Applications", IEEE Transactions on Robotics January 2014; 30(1):103-114.

[SJ2020] https://satijalab.org/costpercell/.

[SO2005] O. Schumacher, S. Mendach, H. Welsch, A. Schramm, C. Heyn, and W. Hansen, "Lithographically defined metal-semiconductor-hybrid nanoscrolls," Applied Physics Letters, vol. 86, no. 14, April 2005.

[SW2019] Wolock, S. L., Lopez, R. & Klein, A. M. Scrublet: computational identification of cell doublets in single-cell transcriptomic data. Cell Syst. 8, 281-291 (2019).

[SW2020] S. Wang and N. Xi, "Calibration of Haptic Sensors Using Transfer Learning," IEEE Sensors Journal, vol. 21, no. 2, pp. 2003-2012, 2020.

[TL2016] Ilicic, T. et al. Classification of low quality cells from single-cell RNA-seq data. Genome Biol. 17, 29 (2016).

[TO2006] T. Ohshiro, and Y. Umezawa, "Complementary base-pair-facilitated electron tunneling for electrically pinpointing complementary nucleobases," Proceedings of the National Academy of Sciences, vol. 103, no. 1, pp. 10-14, 2006.

[TO2012] T. Ohshiro, K. Matsubara, M. Tsutsui, M. Furuhashi, M. Taniguchi, and T. Kawai, "Single-molecule electrical random resequencing of DNA and RNA," Scientific reports, vol. 2, no. 1, pp. 1-7, 2012.

[WA2018] A. Wasfi, F. Awwad, and A. I. Ayesh, "Graphene-based nanopore approaches for DNA sequencing: A literature review," Biosensors & Bioelectronics, vol. 119, pp. 191-203, November 2018.

[WQ2013] Wu, Q., Y. Meng, K. Concha, S. Wang, Y. Li, L. Ma, and S. Fu, "Influence of temperature and humidity on nano-mechanical properties of cellulose nanocrystal films made from switchgrass and cotton," Industrial Crops and Products, Vol. 48, pp. 28-35, (2013).

[WR2016] Wagner, R., R. J. Moon, and A. Raman, "Mechanical properties of cellulose nanomaterials studied by contact resonance atomic force microscopy," Cellulose, Vol. 23, pp. 1031-1041, (2016).

[WY2019] Wen, Y., H. Lu, Y. Shen, and H. Xie, "Nanorobotic Manipulation System for 360° Characterization Atomic Force Microscopy," IEEE Transactions on Industrial Electronics, 2019).

[XG2006] X.-G. Zhang, P. S. Krstić, R. Zikić, J. C. Wells, and M. Fuentes-Cabrera, "First-principles transversal DNA conductance deconstructed," Biophysical journal, vol. 91, no. 1, pp. L04-L06, 2006.

[XN2007] Xi, N., J. Zhang, H. Szu, and G. Li, "Nanorobot assembly of carbon nanotubes for mid-IR sensor," in Independent Component Analyses, Wavelets, Unsupervised Nano-Biomimetic Sensors, and Neural Networks V, p. 65760K, (2007).

[XN2010] Xi, N., K. W. C. Lai, H. Chen, and C. K. M. Fung, "Carbon nanotube-based noncryogenic cooled multispectrum focal plane array," in Infrared Technology and Applications XXXVI, p. 766032, (2010).

[XN2011] Xi, N., B. Song, R. Yang, and K. Lai, "Augmented Reality for Nano Manipulation," in Handbook of Augmented Reality, ed: Springer, 2011, pp. 435-447.

[XN2013] Xi, N; Song, B; Yang, R; Lai, K W C; Chen, H; Qu, C; Chen, L, "Video Rate Atomic Force Microscopy:

Use of compressive scanning for nanoscale video imaging", IEEE Nanotechnology Magazine, Vol. 7, Issue 1, Page(s): 4-8, March 2013.

[YJ2017] Yang J. et. al. Establishment of mouse expanded potential stem cells. Nature. 2017 Oct. 19; 550(7676): 393-397.

[YR2015] Yang, R., B. Song, Z. Sun, K. W. C. Lai, C. K. M. Fung, K. C. Patterson, K. Seiffert-Sinha, A. A. Sinha, and N. Xi, "Cellular level robotic surgery: Nanodissection of intermediate filaments in live keratinocytes," Nanomedicine: Nanotechnology, Biology and Medicine, Vol. 11, pp. 137-145, (2015).

[ZJ2008] Zhang, J., N. Xi, H. Chen, K. W. C. Lai, G. Li, and U. C. Wejinya, "Design, manufacturing, and testing of single-carbon-nanotube-based infrared sensors," IEEE transactions on nanotechnology, Vol. 8, pp. 245-251, (2008).

[ZL2005] L. Zhang, E. Deckhardt, A. Weber, C. Schonenberger, and D. Grutzmacher, "Controllable fabrication of SiGe/Si and SiGe/Si/Cr helical nanobelts," Nanotechnology, vol. 16, no. 6, pp. 655-663, June 2005.

[ZL2006a] L. Zhang, L. X. Dong, D. J. Bell, B. J. Nelson, C. Schönenberger, and D. Grützmacher, "Fabrication and Characterization of Freestanding Si/Cr Micro- and Nanospirals," Microelectronic Engineering, vol. 83, no. 4-9, pp. 1237-1240, April-September 2006.

[ZL2006b] L. Zhang, E. Ruh, D. Grutzmacher, L. X. Dong, D. J. Bell, B. J. Nelson, and C. Schonenberger, "Anomalous coiling of SiGe/Si and SiGe/Si/Cr helical nanobelts," Nano Letters, vol. 6, no. 7, pp. 1311-1317, July 2006.

[ZL2008] L. Zhang, L. X. Dong, and B. J. Nelson, "Ring closure of rolled-up Si/Cr nanoribbons," Applied Physics Letters, vol. 92, no. 14, April 2008.

While the invention is explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims

The invention claimed is:

1. A nano scale robotic system for single cell DNA sequencing of a strand of DNA positioned on a slide, comprising:
    an atomic force microscope (AFM) having an end effector in the form of cantilever with a tip, said AFM engaging in a scanning process causing its cantilever tip to scan over the base pairs of the strand of DNA when the slide is positioned on a sample stage of the AFM;
    a pair of spaced apart electrodes at the tip that make contact with opposite sides of the DNA strand;
    a current measurement system connected to the electrodes that measures the current between bases of the DNA strand; and
    an artificial intelligence-based data analytic system for determining the DNA sequence based on the current from the current measuring system.

2. The nano-scale robotic system of claim 1 wherein the current measurement system is a high precision tunneling current measurement system.

3. The nano-scale robotic system of claim 1 wherein the artificial intelligence based data analytic system utilizes a Generative Adversarial Tri-model (GAT) machining learning scheme.

4. The nano-scale robotic system of claim 1 wherein AFM comprises:
    a first control circuit to move the tip in an XY plane of the slide so as to move along the DNA strip, a laser directing a laser beam so as to reflect off a flat top of the cantilever, a photodetector arranged to receive the beam after it has reflected off the top of the cantilever and to generate a deflection signal based on the change in the reflected light, which correlates to deflections of the cantilever towards or away from the slide in a Z direction, and a second control circuit to move the cantilever in the Z direction based on the deflection signal so as to create a feedback signal that keeps the cantilever at a consistent position above the DNA strand.

5. The nano-scale robotic system of claim 4 wherein the photodetector is a position-sensitive photo diode (PSPD).

6. The nano-scale robotic system of claim 1 wherein the AFM causes the cantilever tip to scan over the base pairs of the strand of DNA by means of a semantic compressive motion control based on a non-vector space control approach, comprising:

an output from the AFM of semantically compressed samples of the actual intensity local scan images of the DNA;

a source of compressed desired intensity local scan images;

a comparator for comparing the compressed desired intensity local scan images and compressed actual intensity local scan images, and producing a difference signal; and a non-vector space controller that receives the difference signal and causes the compressed actual intensity local scan images to converge to the compressed desired intensity local scan images in the space of sets by reducing the difference signal, and wherein an output of the controller causes the AFM to change the compressed actual intensity local scanned images as part of a feedback loop.

7. The nano-scale robotic system of claim 6 wherein the AFM scanning process uses a compressive scan pattern.

8. The nano-scale robotic system of claim 6 wherein during the local scan of images uses a prior knowledge of the content of the images in the semantic compression.

9. The nano-scale robotic system of claim 8 wherein a prior knowledge of the shape of a DNA strand is used in the sematic compression.

10. The nano-scale robotic system of claim 6 wherein the semantic compressive motion control utilizes a sensing matrix learned from a group of images of DNA strands, wherein a sensing matrix training process is conducted through a prevalent deep learning strategy.

11. The nano-scale robotic system of claim 10 wherein non-negative matrix factorization (NMF) representation is used to learn the semantic content of AFM images of DNA strands.

12. A method for forming a sub-10-nm-gap dual-tip AFM cantilever comprising the steps of:

using FIB chemical vapor deposition to cut a cantilever and its supporting base from a commercially available cantilever that is pre-coated with metal layers on both sides (top and bottom) to form lead lines and microelectrodes on a pyramid or cone-shaped tip;

if the cone-shaped tip has a precoated metal layer, using FIB to s separate the pre-coated layer into two parts;

if the cone-shaped tip does not have a precoated metal layer use FIBCVD to directly write electrodes on the side surface with a line width of about 1 μm and a thickness of about 50-100 nm;

milling off the cone-shaped tip using FIB to form two small flat surfaces with a side length of 1 μm-3 μm;

applying FIBCVD or EBID to grow nanotips from the flats and to form a lateral bridge on the top of cylindrical tips; and using a focused highly energetic electron beam to generate a sub-10-nm gap between the cylindrical nanotips by cutting the bridge into two parts at the center.

13. The method for forming a sub-10-nm-gap dual-tip AFM cantilever according to claim 12 wherein, when the commercially available cantilever is not pre-coated with metal, further including the step of sputtering metal on both sides.

14. The method for forming a sub-10-nm-gap dual-tip AFM cantilever according to claim 12 wherein microelectrodes and the lead lines have a width of about 2 μm-5 μm and 20 μm-50 μm, respectively.

15. The method for forming a sub-10-nm-gap dual-tip AFM cantilever according to claim 12 wherein the metal coating is gold.

16. The method for forming a sub-10-nm-gap dual-tip AFM cantilever according to claim 13 wherein the metal coating is gold.

17. The method for forming a sub-10-nm-gap dual-tip AFM cantilevers according to claim 12 wherein, the electron beam has an energy of 200 keV to 300 keV.

18. The method for forming a sub-10-nm-gap dual-tip AFM cantilever according to claim 12 wherein the pyramid or cone-shaped tip is hollow.

19. The method for forming a sub-10-nm-gap dual-tip AFM cantilever according to claim 12 wherein the step of applying FIBCVD or EBID to grow nanotips causes a growth direction of 30° for both sides to tilt towards the inner sides and the cylindrical nanotips have a diameter between 30-50 nm and a length of 1 μm-3 μm.

20. The method for forming a sub-10-nm-gap dual-tip AFM cantilever according to claim 12 wherein the step of using a focused highly energetic electron beam uses CsTEM.

21. A method for forming a sub-10-nm-gap dual-tip AFM cantilever comprising the steps of:

using PECVD to grow a 50-nm thick silicon dioxide ($SiO_2$) thin film;

forming several 50-nm cross cylindrical tips with a smallest gap around 15 nm using an EBL system to pattern the tips on a spin-coated photoresist;

using an e-beam to evaporate about a 45-nm-thickness of Au to develop a pattern;

pressing as-fabricated metal discs from the top using a ns YAG laser, three layers of materials are used for achieving this, including a 4-μm-thick Al layer as a compressor, a graphite one for ablative coating, and a CaF2/ZeSe glass layer for transparent confinement;

using photolithography masks with pre-designed patterns together with UV exposure for both the top and bottom side patterning of the contours of a supporting base and cantilevers using spin coating of photoresist, developing and dry etching of a $SiO_2$ layer using ICP;

creating windows for Si wet etching by using a KOH solution;

forming pyramid tips after etching while the cantilevers are kept with a greater thickness than the final sizes;

growing a 50-nm-thick layer of $SiO_2$ using PECVD on the top surface as an insulating layer for the fabrication of lead out electrodes on the supporting bases and microelectrodes on the cantilevers;

selectively removing the $SiO_2$ on the top of the tips using dry etching with ICP based on UV exposure and developing on a spin coated photoresist layer;

depositing a 45-nm-thick gold film with an e-beam evaporator, to serve as electrodes;
using FIBCVD to directly write a nanoelectrode connecting the microelectrodes on the cantilevers and the tips so that the nanoelectrode follows a path along the pyramid side and top surfaces, thus realizing a 3D electrical connection; and
using BOE to etch the $SiO_2$ away followed by Si etching using KOH.

22. The method for forming a sub-10-nm-gap dual-tip AFM cantilevers according to claim 21 further including the step of laser stamping to shrink the gap further to a sub-10-nm scale.

23. A method for forming a sub-10-nm-gap dual-tip AFM cantilever comprising the steps of:
vapor depositing an insulating layer of $SiO_2$ on both sides of Si wafers using PECVD;
depositing a sacrificial layer of Al film patterned with UV exposure, evaporating the film with an electron beam and subjecting the film to a lift off process to from a self-curling mesa that is a SixNy film with intrinsic stress;
using a UV lithography process to design an exposure mask and ICP etching technology to achieve mesa fabrication;
patterning an Au bottom electrode with UV exposure and electron-beam evaporation;
obtaining a nano-gap insulating layer by using ALD deposition technology to create an $Al_2O_3$ film;
using photoresist as a mask and ICP etching to retain a pattern of the $Al_2O_3$ film above the bottom electrode;
using UV exposure, electron beam vapor deposition and lift off techniques to obtain an Au film top electrode pattern;
using the back jacketing method by pre-etching the backside of the $SiO_2$ layer using photoresist to create etching window patterns;
using ICP etching of the $SiO_2$ to expose the Si etching material and Acetone to remove the etching window photoresist;
using PECVD to vaporize a portion of the $SiO_2$ anti-etching protection layer on the substrate surface;
placing the substrate in a KOH solution at room temperature to etch off the substrate Si;
using UV lithography together with ICP to etch the $SiO_2$ protective layer in order to transfer the etching window pattern to the top of the substrate;
using acetone to remove the etched window photoresist;
using UV exposure to obtain a self-curling release window pattern;
using NMD solution to etch the sacrificial layer Al to gradually release the curling structure;
placing the sample with its self-curling structure in acetone solution to remove the photoresist;
using KOH to etch the silicon substrate at the point where the upper and lower release windows are connected; and
placing the sample in a BOE etching solution to completely etch the exposed $SiO_2$ and then placing it in aqueous solution to rest in order to obtain an AFM probe with a self-curling structure.

24. The method for forming a sub-10-nm-gap dual-tip AFM cantilevers according to claim 23 wherein the sacrificial layer of Al film is a 20-nm-thick, the patterned Au bottom electrode is 50-nm-thick, the nano-gap insulating layer of $Al_2O_3$ film is 1-nm thick, the Au film top electrode pattern is 50 nm thick, and the portion of the $SiO_2$ anti-etching protection is 130 nm thick.

25. A method for nano scale robotic single cell DNA sequencing of a strand of DNA positioned on a slide of an atomic force microscope, which moves an end effector in the form of a cantilever with a tip along the DNA strand, and wherein the spacing between electrodes at the tip is greater than the spacing between the nucleobases of the DNA strand so that the electrical potential difference between the electrodes is the sum of the occupied molecular orbital (HOMO) energy of all of the nucleobases between the two electrodes, comprising the steps of:
preparing a DNA strand for sequencing;
adding the energy value of nine T nucleobases to the beginning and end of the DNA strand;
conducting n-9 measurements as one measurement loop where n is the total number of nucleobases after concatenation of T nucleobases at the beginning and end of the DNA chain,
adding Gaussian noise to the measurement values to account for contact noise between the electrodes and DNA;
adding beta noise to the measurement values to account for errors in the end effector motion;
solving for the DNA sequence with a neural network whose inputs are the position serials of each nucleobase and whose outputs are the HOMO energy values of the nucleobases at the corresponding positions, wherein the loss function for training the neural network is defined as $L=\|Ax-d\|_2^2$, and the best DNA sequence can be determined by minimizing the loss value; and
repeating loops of measurement where the result after the last measurement is used as the initialization of the next calculation; and
continuing to repeat loops of measurement until the there is no change in the generated DNA sequence.

26. The method of claim 25 wherein the Gaussian noise and beta noise are calibrated by the steps of:
measuring several pre-known DNA sequences to determine separate noise values;
creating a new framework based on the Generative Adversarial Tri-model (GAT model) to calibrate the noise distribution, wherein the GAT model includes a machine learning model and an analytical model and takes advantage of the approximate qualitative model to facilitate machine learning so as to reduce the training data demand;
training the machine learning model independently until convergence;
basing the analytical model on any kind of knowledge about the machine learning outputs; and
re-initializing the machine learning models-initialized state based on the corrected outputs and training the machine learning models again until convergence from re-initialized value, whereby the whole process forms a loop and will converge when the machine learning outputs conform to the analytical models to some acceptable degree or vice versa.

27. The method of claim 25 wherein the step of preparing a DNA strand comprises the steps of:
isolating target single cells by mechanical dissociation and/or enzymatic digestion;
extracting genomic DNA;
removing any residual RNA like lncRNA and miRNA, and proteins like histones;
generating linear single-stranded DNA and preventing the reforming of base pairs;

connecting both ends of the strand with known strands so as to tag them with identifiable barcodes; and straightening and fixing the single strand on a flat substrate and keeping all bases in a same orientation.

\* \* \* \* \*